(12) United States Patent
Okada et al.

(10) Patent No.: US 10,338,471 B2
(45) Date of Patent: Jul. 2, 2019

(54) COMPOSITION FOR FORMING UNDERLAYER FILM FOR LITHOGRAPHY, UNDERLAYER FILM FOR LITHOGRAPHY AND PATTERN FORMING METHOD

(71) Applicant: Mitsubishi Gas Chemical Company, Inc., Tokyo (JP)

(72) Inventors: Kana Okada, Kanagawa (JP); Takashi Makinoshima, Kanagawa (JP); Masatoshi Echigo, Kanagawa (JP); Go Higashihara, Okayama (JP); Atsushi Okoshi, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 15/502,456

(22) PCT Filed: Jul. 31, 2015

(86) PCT No.: PCT/JP2015/071855
§ 371 (c)(1),
(2) Date: Feb. 7, 2017

(87) PCT Pub. No.: WO2016/021511
PCT Pub. Date: Feb. 11, 2016

(65) Prior Publication Data
US 2017/0227849 A1 Aug. 10, 2017

(30) Foreign Application Priority Data
Aug. 8, 2014 (JP) ................. 2014-162535

(51) Int. Cl.
| | | |
|---|---|---|
| *G03F 7/038* | (2006.01) |
| *G03F 7/039* | (2006.01) |
| *G03F 7/004* | (2006.01) |
| *G03F 7/16* | (2006.01) |
| *G03F 7/20* | (2006.01) |
| *G03F 7/32* | (2006.01) |
| *H01L 21/02* | (2006.01) |
| *H01L 21/31* | (2006.01) |
| *H01L 21/30* | (2006.01) |
| *C07C 261/02* | (2006.01) |
| *C09D 7/20* | (2018.01) |
| *G03F 7/11* | (2006.01) |
| *H01L 21/027* | (2006.01) |
| *C09D 179/04* | (2006.01) |
| *G03F 7/38* | (2006.01) |
| *H01L 21/308* | (2006.01) |
| *H01L 21/311* | (2006.01) |
| *G03F 7/075* | (2006.01) |
| *G03F 7/09* | (2006.01) |

(52) U.S. Cl.
CPC .............. *G03F 7/11* (2013.01); *C07C 261/02* (2013.01); *C09D 7/20* (2018.01); *C09D 179/04* (2013.01); *G03F 7/0045* (2013.01); *G03F 7/0046* (2013.01); *G03F 7/0392* (2013.01); *G03F 7/0752* (2013.01); *G03F 7/091* (2013.01); *G03F 7/094* (2013.01); *G03F 7/162* (2013.01); *G03F 7/168* (2013.01); *G03F 7/2037* (2013.01); *G03F 7/322* (2013.01); *G03F 7/38* (2013.01); *H01L 21/027* (2013.01); *H01L 21/0274* (2013.01); *H01L 21/3081* (2013.01); *H01L 21/3086* (2013.01); *H01L 21/31116* (2013.01); *H01L 21/31144* (2013.01); *G03F 7/0397* (2013.01)

(58) Field of Classification Search
None
See application file for complete search history.

(56) References Cited

U.S. PATENT DOCUMENTS

| | | | | |
|---|---|---|---|---|
| 3,994,949 A * | 11/1976 | Meyer | ................... | C07C 261/02 560/301 |
| 4,745,215 A * | 5/1988 | Cox | ....................... | C07C 261/02 428/422.8 |
| 5,605,781 A * | 2/1997 | Gelorme | ............ | C08G 73/0655 430/270.1 |
| 2005/0182203 A1* | 8/2005 | Sugano | ................. | C07C 261/02 525/423 |
| 2005/0255712 A1 | 11/2005 | Kato et al. | | |
| 2007/0207410 A1* | 9/2007 | Leatherdale | ......... | G02B 6/1221 430/280.1 |
| 2009/0017316 A1* | 1/2009 | Kato | ....................... | C08L 79/04 428/447 |

(Continued)

FOREIGN PATENT DOCUMENTS

| | | |
|---|---|---|
| EP | 1566377 A | 8/2005 |
| EP | 2219076 A | 8/2010 |

(Continued)

OTHER PUBLICATIONS

Sanshin Chemical Industry Co., Ltd, "Cationic polymerization initiators", copyright 2003.*
International Search Report dated Oct. 27, 2015 for PCT/JP2015/071855 and English translation of the same (5 pages).

*Primary Examiner* — Martin J Angebranndt
(74) *Attorney, Agent, or Firm* — Fitch, Even, Tabin & Flannery LLP

(57) ABSTRACT

The composition for forming an underlayer film for lithography according to the present invention contains a compound represented by a specific formula (1) and 20 to 99% by mass of a solvent component (S), in which 27 to 100% by mass of the compound represented by the formula (1) is included in a component (A) other than the solvent component (S).

11 Claims, No Drawings

(56) References Cited

U.S. PATENT DOCUMENTS

| | | | |
|---|---|---|---|
| 2010/0316950 A1 | 12/2010 | Oguro et al. | |
| 2012/0108071 A1* | 5/2012 | Ogihara | G03F 7/091 438/703 |
| 2012/0171611 A1 | 7/2012 | Ideno et al. | |
| 2014/0227887 A1 | 8/2014 | Kim et al. | |
| 2018/0101097 A1* | 4/2018 | Okada | C08G 73/06 |

FOREIGN PATENT DOCUMENTS

| | | | | |
|---|---|---|---|---|
| EP | 3267256 A | | 1/2018 | |
| EP | 3282319 A | | 2/2018 | |
| JP | 2001-207057 | * | 7/2001 | ............ G03F 7/004 |
| JP | 2001-132810 | * | 11/2001 | ........... G03F 7/0038 |
| JP | 2002-334869 A | | 11/2002 | |
| JP | 2004-177668 A | | 6/2004 | |
| JP | 2004-271838 A | | 9/2004 | |
| JP | 2005-250434 A | | 9/2005 | |
| JP | 2006-193607 A | | 7/2006 | |
| JP | 2006-293207 | * | 10/2006 | |
| JP | 2007-226204 A | | 6/2007 | |
| JP | 2007-226170 A | | 9/2007 | |
| JP | 2010-189470 A | | 9/2010 | |
| JP | 2011-215360 | * | 10/2011 | ............ G03F 7/038 |
| JP | 2012-159590 | * | 8/2012 | ............ G03F 7/004 |
| JP | 2012-212051 A | | 11/2012 | |
| TW | 200925785 A | | 6/2009 | |
| TW | 201319756 A | | 5/2013 | |
| WO | 2004/066377 A1 | | 8/2004 | |
| WO | 2009/072465 A1 | | 6/2009 | |
| WO | 2011/034062 A1 | | 3/2011 | |
| WO | 2013/036027 A1 | | 3/2013 | |
| WO | 2016/140081 | * | 9/2016 | |
| WO | 2016/163457 | * | 10/2016 | |

* cited by examiner

COMPOSITION FOR FORMING UNDERLAYER FILM FOR LITHOGRAPHY, UNDERLAYER FILM FOR LITHOGRAPHY AND PATTERN FORMING METHOD

CROSS-REFERENCE TO RELATED APPLICATIONS

This application is a U.S. national phase application filed under 35 U.S.C. § 371 of International Application PCT/JP2015/071855, filed on Jul. 31, 2015, designating the United States, which claims priority from Japanese Application No. 2014-162535, filed Aug. 8, 2014, which are hereby incorporated herein by reference in their entirety.

TECHNICAL FIELD

The present invention relates to a composition for forming an underlayer film for lithography, containing a compound having a specific structure, an underlayer film for lithography, formed using the composition, and a pattern forming method using the composition.

BACKGROUND ART

Semiconductor devices are manufactured through microfabrication by lithography using a photoresist material, but are required to be made finer by a pattern rule in accordance with the increase in integration degree and the increase in speed of LSI in recent years. In lithography using exposure to light, which is currently used as a general-purpose technique, the resolution is now approaching the intrinsic limitation associated with the wavelength of the light source.

A light source for lithography, for use in forming a resist pattern, has a shorter wavelength from a KrF excimer laser (248 nm) to an ArF excimer laser (193 nm). However, as the resist pattern is made finer and finer, there arise a problem of resolution and a problem of collapse of the resist pattern after development, and therefore there is demanded for making a resist film thinner. If the resist film is merely made thinner in response to such a demand, it is difficult to achieve the resist pattern having a film thickness sufficient for processing a substrate. Accordingly, there is increasingly required a process in which not only the resist pattern but also a resist underlayer film is prepared between a resist and a semiconductor substrate to be processed and the resist underlayer film is allowed to have a function as a mask at the time of processing the substrate.

Currently, as the resist underlayer film for such a process, various ones are known. Examples can include a resist underlayer film for lithography, having a selection ratio of dry etching rate close to the resist, unlike a conventional resist underlayer film having a high etching rate. As the material for forming such a resist underlayer film for lithography, there has been proposed a material for forming an underlayer film for multilayer resist process, containing a resin component having at least a substituent which releases a terminal group to form a sulfonic acid residue when a predetermined energy is applied, and a solvent (see, for example, Patent Literature 1). In addition, examples can include a resist underlayer film for lithography, having a smaller selection ratio of dry etching rate than the resist. As the material for forming such a resist underlayer film for lithography, there has been proposed a resist underlayer film material including a polymer having a specific repeating unit (see, for example, Patent Literature 2). Furthermore, examples can include a resist underlayer film for lithography, having a smaller selection ratio of dry etching rate than the semiconductor substrate. As the material for forming such a resist underlayer film for lithography, there has been proposed a resist underlayer film material including a polymer formed by co-polymerizing a repeating unit of acenaphthylene, and a substituted or non-substituted repeating unit having a hydroxy group (see, for example, Patent Literature 3).

On the other hand, as a material for allowing such a resist underlayer film to have a high etching resistance, an amorphous carbon underlayer film is well known, which is formed by CVD using methane gas, ethane gas, acetylene gas, or the like as a raw material.

In addition, as a material that is excellent in optical characteristics and etching resistance and that is capable of being dissolved in a solvent and being applied to a wet process, the present inventors have proposed a composition for forming an underlayer film for lithography (see, for example, Patent Literature 4 and Patent Literature 5), which contains a naphthalene formaldehyde polymer including a specific constituent unit, and an organic solvent.

Meanwhile, with respect to a forming method of an intermediate layer for use in forming a resist underlayer film in a three-layer process, for example, known are a forming method of a silicon nitride film (see, for example, Patent Literature 6), and a CVD forming method of a silicon nitride film (see, for example, Patent Literature 7). In addition, as an intermediate layer material for a three-layer process, known is a material containing a silsesquioxane-based silicon compound (see, for example, Patent Literature 8 and Patent Literature 9).

CITATION LIST

Patent Literature

Patent Literature 1: Japanese Patent Laid-Open No. 2004-177668
Patent Literature 2: Japanese Patent Laid-Open No. 2004-271838
Patent Literature 3: Japanese Patent Laid-Open No. 2005-250434
Patent Literature 4: International Publication No. WO 2009/072465
Patent Literature 5: International Publication No. WO 2011/034062
Patent Literature 6: Japanese Patent Laid-Open No. 2002-334869
Patent Literature 7: International Publication No. WO 2004/066377
Patent Literature 8: Japanese Patent Laid-Open No. 2007-226170
Patent Literature 9: Japanese Patent Laid-Open No. 2007-226204

SUMMARY OF INVENTION

As described above, many materials for forming an underlayer film for lithography have been conventionally proposed, but there are no ones that not only have such a high solvent solubility as to be able to be applied to a wet process such as a spin coating method or screen printing, but also simultaneously satisfy heat resistance and etching resistance at a high level, and thus a new material is required to be developed.

The present invention has been made in view of the above problem, and an object thereof is to provide a composition for forming an underlayer film for lithography, which can be applied to a wet process and which is excellent in heat resistance and etching resistance, and a pattern forming method using the composition.

The present inventors have intensively studied to solve the above problem, and as a result, have found that the above problem can be solved by using a compound having a specific structure in a specific amount, thereby leading to the completion of the present invention. That is, the present invention is as follows.

[1]

A composition for forming an underlayer film for lithography, comprising:

a compound represented by the following formula (1) and 20 to 99% by mass of a solvent component (S), wherein 27 to 100% by mass of the compound represented by the formula (1) is comprised in a component (A) other than the solvent component (S).

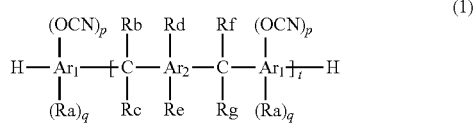
(1)

(in formula (1), each of $Ar_1$ and $Ar_2$ independently represents a benzene structure, a naphthalene structure or a biphenyl structure, each Ra independently represents a hydrogen atom, an alkyl group having 1 to 6 carbon atoms, an aryl group having 6 to 12 carbon atoms, an alkoxy group having 1 to 4 carbon atoms, or a group in which an alkyl group having 1 to 6 carbon atoms is bonded to an aryl group having 6 to 12 carbon atoms, each of Rb, Rc, Rf and Rg independently represents a hydrogen atom, an alkyl group having 1 to 6 carbon atoms or an aryl group having 6 to 12 carbon atoms, each of Rd and Re independently represents a hydrogen atom, an alkyl group having 1 to 6 carbon atoms, an aryl group having 6 to 12 carbon atoms, an alkoxy group having 1 to 4 carbon atoms or a hydroxy group, wherein a position of a substituent on each of $Ar_1$ and $Ar_2$ can be arbitrarily selected, p represents the number of cyanate group(s) bonded and is an integer of 1 to 3, q represents the number of Ra bonded and is 4−p when $Ar_1$ represents the benzene structure, 6−p when $Ar_1$ represents the naphthalene structure, or 8−p when $Ar_1$ represents the biphenyl structure, and t represents an integer of 1 to 50.)

[2]

The composition for forming the underlayer film for lithography according to [1], wherein the compound represented by the formula (1) is a compound represented by the following formula (2).

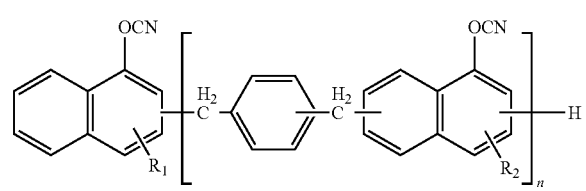
(2)

(in formula (2), each of $R_1$ and $R_2$ independently represents a hydrogen atom or an alkyl group having 1 to 6 carbon atoms, and may be the same or different, wherein a position of each of $R_1$ and $R_2$ on the aromatic ring can be arbitrarily selected, and n represents an integer of 1 to 50.)

[3]

The composition for forming the underlayer film for lithography according to [1], wherein the compound represented by the formula (1) is a compound represented by the following formula (3).

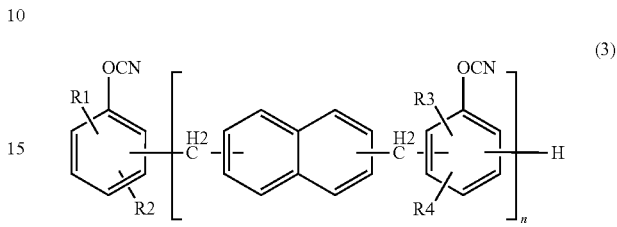
(3)

(in formula (3), each of $R_1$ to $R_4$ independently represents a hydrogen atom or an alkyl group having 1 to 6 carbon atoms, and may be the same or different, and n represents an integer of 1 to 50.)

[4]

The composition for forming the underlayer film for lithography according to [1], wherein the compound represented by the formula (1) is a compound represented by the following formula (4).

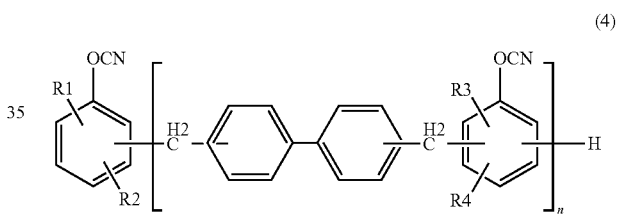
(4)

(in formula (4), each of $R_1$ to $R_4$ independently represents a hydrogen atom or an alkyl group having 1 to 6 carbon atoms, and may be the same or different, and n represents an integer of 1 to 50.)

[5]

The composition for forming the underlayer film for lithography according to [2], wherein the compound represented by the formula (2) is a compound represented by the following formula (5).

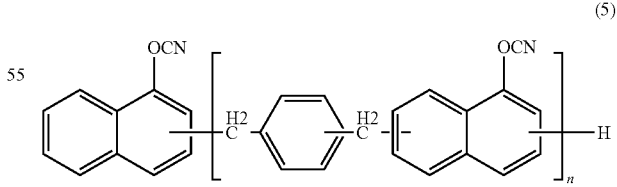
(5)

(in formula (5), n represents an integer of 1 to 50.)

[6]

The composition for forming the underlayer film for lithography according to [3], wherein the compound represented by the formula (3) is a compound represented by the following formula (6).

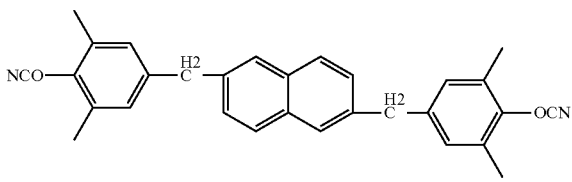

(6)

[7]

The composition for forming the underlayer film for lithography according to [4], wherein the compound represented by the formula (4) is a compound represented by the following formula (7).

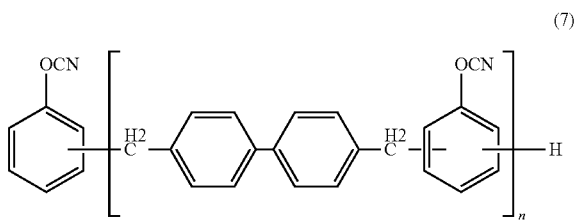

(7)

(in formula (7), n represents an integer of 1 to 50.)

[8]

The composition for forming the underlayer film for lithography according to any of [1] to [7], wherein the component (A) further comprises an acid generating agent.

[9]

The composition for forming the underlayer film for lithography according to any of [1] to [8], wherein the component (A) further comprises a crosslinking agent.

[10]

An underlayer film for lithography, formed using the composition for forming the underlayer film for lithography according to any of [1] to [9].

[11]

A resist pattern forming method comprising step (A-1) of forming an underlayer film on a substrate by using the composition for forming the underlayer film according to any of [1] to [9], step (A-2) of forming at least one photoresist layer on the underlayer film, and step (A-3) of, after step (A-2), irradiating a predetermined region of the photoresist layer with radiation, followed by developing.

[12]

A circuit pattern forming method comprising step (B-1) of forming an underlayer film on a substrate by using the composition for forming the underlayer film according to any of [1] to [9], step (B-2) of forming an intermediate layer film on the underlayer film by using a silicon atom-containing resist intermediate layer film material, step (B-3) of forming at least one photoresist layer on the intermediate layer film, step (B-4) of, after step (B-3), irradiating a predetermined region of the photoresist layer with radiation, followed by developing to form a resist pattern, and step (B-5) of, after step (B-4), etching the intermediate layer film with the resist pattern as a mask, etching the underlayer film with an obtained intermediate layer film pattern as an etching mask and etching the substrate with an obtained underlayer film pattern as an etching mask, to form a pattern on the substrate.

The composition for an underlayer film for lithography of the present invention can be applied to a wet process and is excellent in heat resistance and etching resistance.

DESCRIPTION OF EMBODIMENTS

Hereinafter, an embodiment (hereinafter, referred to as "the present embodiment") of the present invention will be described. It is to be noted that the present embodiments are illustrative for describing the present invention, and the present invention is not limited only to the present embodiments.

[Composition for Forming Underlayer Film for Lithography]

A composition for forming an underlayer film for lithography of the present embodiment contains a compound represented by the following formula (1) and 20 to 99% by mass of a solvent component (S), in which 27 to 100% by mass of the compound represented by the formula (1) is included in a component (A) other than the solvent component (S).

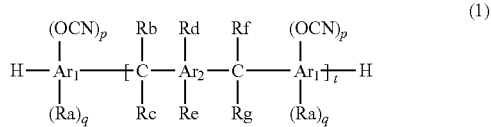

(1)

(in formula (1), each of $Ar_1$ and $Ar_2$ independently represents a benzene structure, a naphthalene structure or a biphenyl structure, each Ra independently represents a hydrogen atom, an alkyl group having 1 to 6 carbon atoms, an aryl group having 6 to 12 carbon atoms, an alkoxy group having 1 to 4 carbon atoms, or a group in which an alkyl group having 1 to 6 carbon atoms is bonded to an aryl group having 6 to 12 carbon atoms, each of Rb, Rc, Rf and Rg independently represents a hydrogen atom, an alkyl group having 1 to 6 carbon atoms or an aryl group having 6 to 12 carbon atoms, each of Rd and Re independently represents a hydrogen atom, an alkyl group having 1 to 6 carbon atoms, an aryl group having 6 to 12 carbon atoms, an alkoxy group having 1 to 4 carbon atoms or a hydroxy group, wherein the position of a substituent on each of $Ar_1$ and $Ar_2$ can be arbitrarily selected, p represents the number of cyanate group(s) bonded and is an integer of 1 to 3, q represents the number of Ra bonded and is 4−p when $Ar_1$ represents the benzene structure, 6−p when $Ar_1$ represents the naphthalene structure, or 8−p when $Ar_1$ represents the biphenyl structure, and t represents an integer of 1 to 50.)

The composition for forming an underlayer film for lithography of the present embodiment has such a configuration, and therefore can be applied to a wet process and is excellent in heat resistance and etching resistance. Herein, the composition for forming an underlayer film for lithography of the present embodiment contains a compound having not only an aromatic structure, but also a cyanate group, and the cyanate group even by itself allows a crosslinking reaction thereof to occur due to high-temperature baking, thereby allowing a high heat resistance to be exhibited. As a result, an underlayer film can be formed which is inhibited from being degraded at high-temperature baking and which is also excellent in etching resistance to oxygen plasma etching or the like. Furthermore, the composition for forming an underlayer film for lithography of the present embodiment has a high solubility in an organic solvent, has a high solubility in a safe solvent and has a good product quality stability, regardless of having an aromatic structure. Additionally, the composition for an underlayer film for lithography of the present embodiment is also excellent in adhesiveness with a resist layer and a resist intermediate layer film material, and therefore can provide an excellent resist pattern.

The content of the compound represented by the following formula (1) in the component (A) is 27 to 100% by mass, preferably 30 to 100% by mass, more preferably 50 to 100% by mass, further preferably 70 to 100% by mass, still more preferably 90 to 100% by mass in terms of heat resistance and etching resistance. In addition, the content of the compound represented by the following formula (1) in the component (A) is particularly preferably 100% by mass from the viewpoint of a reduction in heat weight loss.

In addition, the content of the compound represented by the following formula (1) in the composition for forming an underlayer film for lithography of the present embodiment is preferably 1 to 80% by mass, more preferably 1 to 50% by mass, further preferably 2 to 40% by mass, still more preferably 2 to 20% by mass in terms of solubility and coatability.

[Compound Represented by Formula (1)]

The compound for use in the composition for forming an underlayer film for lithography of the present embodiment is a cyanate-based compound represented by the formula (1). In the compound represented by the formula (1), each of $Ar_1$ and $Ar_2$ independently represents a benzene structure, a naphthalene structure or a biphenyl structure.

In the compound represented by the formula (1), each Ra independently represents a hydrogen atom, an alkyl group having 1 to 6 carbon atoms, an aryl group having 6 to 12 carbon atoms, an alkoxy group having 1 to 4 carbon atoms, or a group in which an alkyl group having 1 to 6 carbon atoms is bonded to an aryl group having 6 to 12 carbon atoms. Here, the position of Ra on the aromatic ring can be arbitrarily selected.

Examples of the alkyl group having 1 to 6 carbon atoms include, but not limited to the following, a methyl group, an ethyl group, an isopropyl group, a n-butyl group, an i-butyl group, a tert-butyl group, and an isomeric pentyl group.

Examples of the aryl group having 6 to 12 carbon atoms include, but not limited to the following, a phenyl group, a naphthyl group, and a biphenyl group.

Examples of the alkoxy group having 1 to 4 carbon atoms include, but not limited to the following, a methoxy group, an ethoxy group, a propoxy group, and a butoxy group.

Examples of the group, in which an alkyl group having 1 to 6 carbon atoms is bonded to an aryl group having 6 to 12 carbon atoms, include, but not limited to the following, an alkylphenyl group having the alkyl, such as a tolyl group, an alkylnaphthyl group having the alkyl group, such as a methylnaphthyl group, an alkylbiphenyl group having the alkyl group, such as a methylbiphenyl group, an arylmethyl group having the aryl, such as a benzyl group, an arylethyl group having the aryl, such as a naphthylethyl group, and an arylpropyl group having the aryl, such as a biphenylpropyl group.

In the compound represented by the formula (1), each of Rb, Rc, Rf and Rg independently represents a hydrogen atom, an alkyl group having 1 to 6 carbon atoms or an aryl group having 6 to 12 carbon atoms. Specific examples of the alkyl group having 1 to 6 carbon atoms and the aryl group having 6 to 12 carbon atoms include, but not particularly limited to, the same groups as described above.

Each of Rd and Re independently represents a hydrogen atom, an alkyl group having 1 to 6 carbon atoms, an aryl group having 6 to 12 carbon atoms, an alkoxy group having 1 to 4 carbon atoms, or a hydroxy group. Specific examples of the alkyl group having 1 to 6 carbon atoms, the aryl group having 6 to 12 carbon atoms, and the alkoxy group having 1 to 4 carbon atoms include, but not particularly limited to, the same groups as described above.

In the compound represented by the formula (1), p represents the number of cyanate group(s) bonded and is an integer of 1 to 3; and q represents the number of Ra bonded and is 4–p when $Ar_1$ represents a benzene structure, 6–p when $Ar_1$ represents a naphthalene structure, or 8–p when $Ar_1$ represents a biphenyl structure.

In the compound represented by the formula (1), t represents an integer of 1 to 50, and t is preferably an integer of 1 to 40, more preferably an integer of 1 to 30, particularly preferably an integer of 1 to 10. In addition, the composition for forming an underlayer film for lithography of the present embodiment may also include a mixture of compounds having different t.

The molecular weight of the compound represented by the formula (1) is not particularly limited, and the weight average molecular weight (Mw) in terms of polystyrene is preferably 500 to 300,000, and more preferably 550 to 200,000. In addition, the compound having the structure represented by the formula (1) preferably has a dispersity (weight average molecular weight Mw/number average molecular weight Mn) in a range from 1.1 to 7, and more preferably in a range from 1.1 to 5 from the viewpoints of improving a crosslinking efficiency and suppressing a volatile component during baking. Herein, the Mw, the Mn and the dispersity can be determined by a method in Examples described later.

The compound represented by the formula (1) preferably has a high solubility in a solvent from the viewpoint of making application of a wet process easier. Specifically, when 1-methoxy-2-propanol (PGME) and/or propylene glycol monomethyl ether acetate (PGMEA) are/is used for the solvent, the compound represented by the formula (1) of the present embodiment preferably has a solubility of 10% by mass or more in the solvent. Herein, the solubility in PGME and/or PGMEA is defined as "Mass of compound/(Mass of compound+Mass of solvent)×100 (% by mass)". For example, in the case where 10 g of the compound is evaluated to be dissolved in 90 g of PGMEA, the solubility of the material for forming an underlayer film in PGMEA is "10% by mass or more", and in the case where the compound is evaluated not to be dissolved, the solubility is "less than 10% by mass".

As the compound represented by the formula (1), any compound represented by formulae (2) to (4) is preferable and any compound represented by formulae (5) to (7) is more preferable in terms of availability and economic efficiency of a raw material.

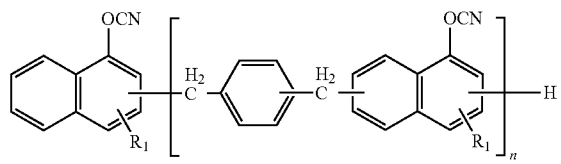

(2)

(in formula (2), each of $R_1$ and $R_2$ independently represents a hydrogen atom or an alkyl group having 1 to 6 carbon atoms, and may be the same or different, n represents an integer of 1 to 50, and the position of each of $R_1$ and $R_2$ on the aromatic ring can be arbitrarily selected.)

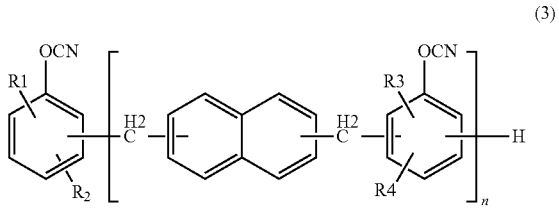

(3)

(in formula (3), each of $R_1$ to $R_4$ independently represents a hydrogen atom or an alkyl group having 1 to 6 carbon atoms, and may be the same or different, and n represents an integer of 1 to 50.)

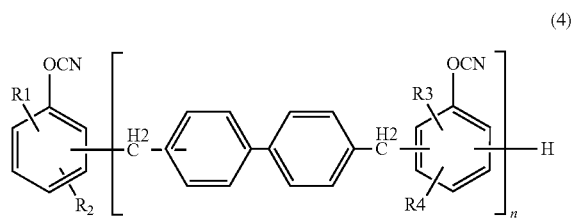

(4)

(in formula (4), each of $R_1$ to $R_4$ independently represents a hydrogen atom or an alkyl group having 1 to 6 carbon atoms, and may be the same or different, and n represents an integer of 1 to 50.)

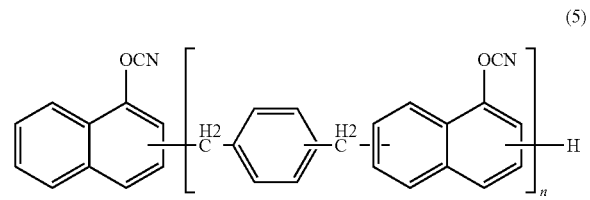

(5)

(in formula (5), n represents an integer of 1 to 50.)

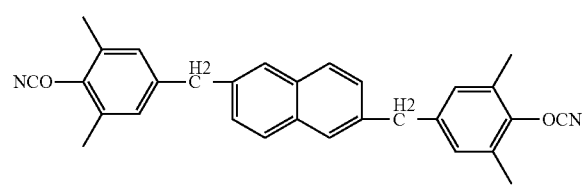

(6)

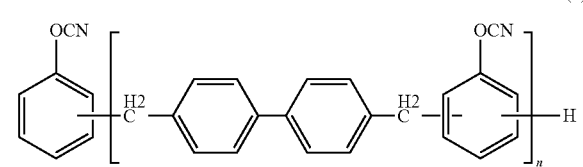

(7)

(in formula (7), n represents an integer of 1 to 50.)

[Method for Producing Compound Represented by Formula (1)]

The compound represented by the formula (1) (cyanic acid ester compound) for use in the present embodiment is obtained by cyanation of a hydroxy group of a hydroxy-substituted aromatic compound represented by the following general formula (8), for example. The cyanation method is not particularly limited, and a known method can be applied.

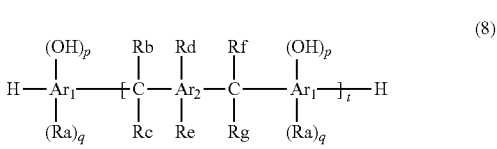

(8)

In the formula (8), $Ar_1$, $Ar_2$, Ra, Rb, Rc, Rd, Re, Rf, Rg, q and t are the same as in the formula (1); and p represents the number of hydroxy group(s) bonded.

Specifically, known are a method in which a hydroxy-substituted aromatic compound and cyanogen halide are reacted in a solvent in the presence of a basic compound; a method in which a hydroxy-substituted aromatic compound and cyanogen halide are reacted in a solvent in the presence of a base with the cyanogen halide being constantly present more excessively than the base (see, for example, U.S. Pat. No. 3,553,244); a method in which, while tertiary amine is used as a base and is more excessively used than cyanogen halide, the tertiary amine is added and thereafter the cyanogen halide is dropped, or the cyanogen halide and the tertiary amine are simultaneously injected and dropped to a hydroxy-substituted aromatic compound in the presence of a solvent (see, for example, Japanese Patent No. 3319061); a method in which a hydroxy-substituted aromatic compound, a trialkylamine and cyanogen halide are reacted in a continuous plug flow system (see, for example, Japanese Patent No. 3905559); a method in which tert-ammonium halide obtained as a by-product in a reaction of a hydroxy-substituted aromatic compound and cyanogen halide in a non-aqueous solution in the presence of tert-amine is treated with a pair of cation and anion (see, for example, Japanese Patent No. 4055210); a method in which a hydroxy-substituted aromatic compound is reacted with tertiary amine and cyanogen halide simultaneously added, in the presence of a solvent that can be separated from water, thereafter the resultant is washed with water for liquid separation, and a reaction product is precipitated in and purified from the resulting solution by using a poor solvent such as secondary or tertiary alcohols, or hydrocarbons (see, for example, Japanese Patent No. 2991054); a method in which a hydroxy-substituted aromatic compound, cyanogen halide and tertiary amine are reacted in a binary phase solvent of water and an organic solvent under an acidic condition (see, for example, Japanese Patent No. 5026727), and the like, and in the present embodiment, such a method can be suitably used to provide the compound represented by the formula (1) (cyanic acid ester compound).

When the method in which the hydroxy-substituted aromatic compound and the cyanogen halide are reacted in a solvent in the presence of a basic compound is used, it is preferable that the hydroxy-substituted aromatic compound as a reactant be dissolved in either a cyanogen halide solution or a basic compound solution in advance and thereafter the cyanogen halide solution and the basic compound solution be brought into contact with each other.

Examples of the method for bringing the cyanogen halide solution and the basic compound solution into contact with each other include (A) a method in which the basic compound solution is injected into the cyanogen halide solution stirred and mixed, (B) a method in which the cyanogen halide solution is injected into the basic compound solution stirred and mixed, (C) a method in which the cyanogen halide solution and the basic compound solution are fed continuously alternately or simultaneously. Among the methods (A) to (C), the method (A) is preferably performed from the viewpoint that a side reaction can be suppressed to allow a higher-purity cyanic acid ester compound to be obtained at a high yield.

In addition, the method for bringing the cyanogen halide solution and the basic compound solution into contact with each other can be performed in any of a semi-batch system or a continuous flow system.

In particular, when the method (A) is used, the basic compound is preferably injected in divisions from the viewpoints that the reaction can be completed without any remaining hydroxy group of the hydroxy-substituted aromatic compound and a higher-purity cyanic acid ester compound can be obtained at a high yield. The number of divisions is not particularly limited and is preferably 1 to 5. In addition, the type of the basic compound may be the same or different with respect to every division.

Examples of the cyanogen halide include, but not limited to the following, cyanogen chloride and cyanogen bromide. As the cyanogen halide, cyanogen halide obtained by a known production method such as a method for reacting hydrogen cyanide or metal cyanide with halogen may be used, or a commercially available product may be used. In addition, a reaction solution containing cyanogen halide obtained by the reaction of hydrogen cyanide or metal cyanide with halogen can also be used as it is.

The amount of the cyanogen halide to be used in the cyanation step relative to the hydroxy-substituted aromatic compound can be usually 0.5 to 5 mol, and is preferably 1.0 to 3.5 mol, based on 1 mol of the hydroxy group of the hydroxy-substituted aromatic compound. When such an amount to be used is adopted, the unreacted hydroxy-substituted aromatic compound can be effectively prevented from remaining, and the yield of the cyanic acid ester compound tends to be more increased.

The solvent for use in the cyanogen halide solution is not limited to the following, and can be any of ketone-based solvents such as acetone, methyl ethyl ketone and methyl isobutyl ketone, aliphatic solvents such as n-hexane, cyclohexane, isooctane, cyclohexanone, cyclopentanone and 2-butanone, aromatic solvents such as benzene, toluene and xylene, ether-based solvents such as diethyl ether, dimethyl cellosolve, diglyme, tetrahydrofuran, methyltetrahydrofuran, dioxane and tetraethylene glycol dimethyl ether, halogenated hydrocarbon-based solvents such as dichloromethane, chloroform, carbon tetrachloride, dichloroethane, trichloroethane, chlorobenzene and bromobenzene, alcohol-based solvents such as methanol, ethanol, isopropanol, methyl cellosolve and propylene glycol monomethyl ether, aprotic polar solvents such as N,N-dimethylformamide, N-methylpyrrolidone, 1,3-dimethyl-2-imidazolidone and dimethyl sulfoxide, nitrile-based solvents such as acetonitrile and benzonitrile, nitro-based solvents such as nitromethane and nitrobenzene, ester-based solvents such as ethyl acetate and ethyl benzoate, hydrocarbon-based solvents such as cyclohexane, a water solvent, and the like. Such solvents can be used singly or in combinations of two or more thereof depending on the reactant.

The basic compound for use in the cyanation step is not particularly limited, and any of an organic base and an inorganic base can be used.

The organic base is not particularly limited, but is preferably any tertiary amine such as trimethylamine, triethylamine, tri-n-butylamine, triamylamine, diisopropylethylamine, diethyl-n-butylamine, methyl di-n-butylamine, methylethyl-n-butylamine, dodecyldimethylamine, tribenzylamine, triethanolamine, N,N-dimethylaniline, N,N-diethylaniline, diphenylmethylamine, pyridine, diethylcyclohexylamine, tricyclohexylamine, 1,4-diazabicyclo[2.2.2]octane, 1,8-diazabicyclo[5.4.0]-7-undecene and 1,5-diazabicyclo[4.3.0]-5-nonene. Among them, trimethylamine, triethylamine, tri-n-butylamine and diisopropylethylamine are more preferable, and triethylamine is further preferable because of providing the intended product at a good yield.

The amount of the organic base to be used can be usually 0.1 to 8 mol and is preferably 1.0 to 3.5 mol, based on 1 mol of the hydroxy group of the hydroxy-substituted aromatic compound. When such an amount to be used is adopted, the unreacted hydroxy-substituted aromatic compound can be effectively prevented from remaining, and the yield of the cyanic acid ester compound tends to be more increased.

The inorganic base is not particularly limited, but is preferably an alkali metal hydroxide. Examples of the alkali metal hydroxide include, but not particularly limited to, sodium hydroxide, potassium hydroxide and lithium hydroxide industrially commonly used. Sodium hydroxide is more preferable because of being inexpensively available.

The amount of the inorganic base to be used can be usually 1.0 to 5.0 mol and is preferably 1.0 to 3.5 mol, based on 1 mol of the hydroxy group of the hydroxy-substituted aromatic compound. When such an amount to be used is adopted, the unreacted hydroxy-substituted aromatic compound can be effectively prevented from remaining, and the yield of the cyanic acid ester compound tends to be more increased.

The basic compound can be used as a solution thereof in a solvent, as described above. The solvent is not particularly limited, and an organic solvent or water can be used therefor.

When the hydroxy-substituted aromatic compound is dissolved in the basic compound solution, the amount of the solvent for use in the basic compound solution can be usually 0.1 to 100 parts by mass and is preferably 0.5 to 50 parts by mass, based on 1 part by mass of the hydroxy-substituted aromatic compound.

When the hydroxy-substituted aromatic compound is not dissolved in the basic compound solution, the amount of the solvent for use in the basic compound solution can be usually 0.1 to 100 parts by mass and is preferably 0.25 to 50 parts by mass, based on 1 part by mass of the basic compound.

An organic solvent for dissolving the basic compound is preferably used when the basic compound is the organic base, and the organic solvent can be appropriately selected from, but not limited to the following: ketone-based solvents such as acetone, methyl ethyl ketone and methyl isobutyl ketone, aromatic solvents such as benzene, toluene and xylene, ether-based solvents such as diethyl ether, dimethyl cellosolve, diglyme, tetrahydrofuran, methyltetrahydrofuran, dioxane and tetraethylene glycol dimethyl ether, halogenated hydrocarbon-based solvents such as dichloromethane, chloroform, carbon tetrachloride, dichloroethane, trichloroethane, chlorobenzene and bromobenzene, alcohol-based solvents such as methanol, ethanol, isopropanol, methyl cellosolve and propylene glycol monomethyl ether, aprotic polar solvents such as N,N-dimethylformamide, N-methylpyrrolidone, 1,3-dimethyl-2-imidazolidone and dimethyl sulfoxide, nitrile-based solvents such as acetonitrile and benzonitrile, nitro-based solvents such as nitromethane and nitrobenzene, ester-based solvents such as ethyl acetate and ethyl benzoate, hydrocarbon-based solvents such as cyclohexane; depending on the basic compound, the reactant, and the solvent for use in the reaction. Such solvents can be used singly or in combinations of two or more thereof.

Water for dissolving the basic compound is preferably used when the basic compound is the inorganic base, and such water may be tap water, distilled water or deionized water without particular limitation. Distilled water or deionized water having few impurities is preferably used in order that the intended cyanic acid ester compound is efficiently obtained.

When the solvent for use in the basic compound solution is water, a catalytic amount of the organic base is preferably used as a surfactant from the viewpoint that the reaction rate is ensured. In particular, a tertiary amine less causing a side reaction is preferable. The tertiary amine is not particularly limited and may be any of alkylamine, arylamine and cycloalkylamine, and specific examples thereof include trimethylamine, triethylamine, tri-n-butylamine, triamylamine, diisopropylethylamine, diethyl-n-butylamine, methyl di-n-butylamine, methylethyl-n-butylamine, dodecyldimethylamine, tribenzylamine, triethanolamine, N,N-dimethylaniline, N,N-diethylaniline, diphenylmethylamine, pyridine, diethylcyclohexylamine, tricyclohexylamine, 1,4-diazabicyclo[2.2.2]octane, 1,8-diazabicyclo[5.4.0]-7-undecene and 1,5-diazabicyclo[4.3.0]-5-nonene. Among them, trimethylamine, triethylamine, tri-n-butylamine and diisopropylethylamine are more preferable, and triethylamine is further preferable because of being high in solubility in water and providing the intended product at a good yield.

The amount of the entire solvent for use in the cyanation step is preferably 2.5 to 100 parts by mass based on 1 part by mass of the hydroxy-substituted aromatic compound from the viewpoint that the hydroxy-substituted aromatic compound is uniformly dissolved to allow the cyanic acid ester compound to be efficiently produced.

In the cyanation step, the pH of the reaction solution is not particularly limited, but the reaction is preferably performed with the pH being kept at less than 7. The pH can be suppressed at less than 7 to thereby inhibit by-products such as imide carbonate and a polymer of the cyanic acid ester compound from being produced, and therefore the cyanic acid ester compound tends to be efficiently produced. A method of adding an acid is preferable for keeping the pH of the reaction solution at less than 7, and it is preferable in such a method that an acid be added to the cyanogen halide solution immediately before the cyanation step or an acid be added to the reaction system with the pH being appropriately measured by a pH meter during the reaction so that the pH is kept at less than 7. Examples of the acid used here include, but not limited to the following, inorganic acids such as hydrochloric acid, nitric acid, sulfuric acid and phosphoric acid, and organic acids such as acetic acid, lactic acid and propionic acid.

The reaction temperature in the cyanation step can be usually −20 to 50° C., and is preferably −15 to 15° C., more preferably −10 to 10° C. from the viewpoints that by-products such as imide carbonate, a polymer of the cyanic acid ester compound, and dialkyl cyanamide are inhibited from being produced, that the reaction solution is inhibited from being condensed, and that, when cyanogen chloride is used as the cyanogen halide, the cyanogen chloride is inhibited from being volatilized.

The reaction pressure in the cyanation step may be normal pressure or increased pressure. If necessary, an inert gas such as nitrogen, helium or argon may be allowed to flow into the system.

In addition, the reaction time is not particularly limited, but the injection time in the case of any of the methods (A) and (B) as the contact method, and the contact time in the case of the method (C) as the contact method are preferably 1 minute to 20 hours, more preferably 3 minutes to 10 hours. Thereafter, stirring is preferably conducted for additional 10 minutes to 10 hours with the reaction temperature being kept. Such a reaction time range tends to allow the intended cyanic acid ester compound to be more economically and industrially obtained.

The degree of progress of the reaction in the cyanation step can be analyzed by liquid chromatography, an IR spectrum method or the like. Volatile components such as dicyanogen and dialkyl cyanamide as by-products can be analyzed by gas chromatography.

After completion of the reaction, a usual post-treatment operation, and, if desired, a separation/purification operation can be performed to thereby isolate the intended cyanic acid ester compound. Specifically, an organic solvent layer including the cyanic acid ester compound may be separated from the reaction solution, and washed with water and thereafter subjected to concentration, precipitation or crystallization, or washed with water and thereafter subjected to solvent replacement. In washing, in order to remove excessive amines, a method in which an acidic aqueous solution such as dilute hydrochloric acid is used is also adopted. In order to remove the water content from the reaction solution sufficiently washed, a drying operation can be performed by a common method using sodium sulfate, magnesium sulfate or the like. In concentration and solvent replacement, in order to suppress polymerization of the cyanic acid ester compound, the organic solvent is distilled off with heating to a temperature of 90° C. or lower under reduced pressure. In precipitation or crystallization, a solvent low in solubility can be used. For example, a method can be adopted in which an ether-based solvent, a hydrocarbon-based solvent such as hexane, or an alcohol-based solvent is dropped or reversely injected to the reaction solution. In order to wash the resulting crude product, a method can be adopted in which a concentrate or a crystal precipitated of the reaction solution is washed with an ether-based solvent, a hydrocarbon-based solvent such as hexane, or an alcohol-based solvent. The reaction solution can be concentrated to provide a crystal, and the crystal can be dissolved again and re-crystallized. In addition, when crystallization is performed, the reaction solution may be simply concentrated or cooled.

[Purification Method of Compound Represented by Formula (1)]

The compound represented by the formula (1) may be if necessary further purified in order to further enhance purity and reduce the amount of the remaining metal. In addition, from the viewpoint of reducing deterioration in storage stability of a composition for forming an underlayer film for lithography due to the remaining of an acid catalyst and a co-catalyst, and deterioration in sensitivity of a composition for forming an underlayer film for lithography due to the remaining of a basic catalyst, purification for the purpose of reductions in the amounts of the remaining catalyst may be performed.

Such purification can be performed by a known method as long as the compound represented by the formula (1) is not modified, and examples include, but are not particularly limited to, a method of washing with water, a method of washing with an acidic aqueous solution, a method of washing with a basic aqueous solution, a method of treating with an ion exchange resin, and a method of treating with silica gel column chromatography. These purification methods are preferably performed in combinations of two or more. The purification method of washing with an acidic aqueous solution will be described later in detail.

The acidic aqueous solution, the basic aqueous solution, the ion exchange resin and the silica gel column chromatography are not particularly limited, and can be appropriately selected optimally depending on the metal to be removed, the amount(s) and the type(s) of an acidic compound and/or a basic compound, the type of the compound represented by the formula (1), to be purified, and the like. Examples of the acidic aqueous solution include an aqueous solution of hydrochloric acid, nitric acid or acetic acid, having a concentration of 0.01 to 10 mol/L, examples of the basic aqueous solution include an aqueous ammonia solution having a concentration of 0.01 to 10 mol/L, and examples of the ion exchange resin include a cation exchange resin such as Amberlyst 15J-HG Dry produced by Organo Corporation.

Drying may also be performed after the above purification. Such drying can be performed by a known method, and examples thereof include, but are not particularly limited to, a vacuum drying method or a hot air drying method in a condition where the compound represented by the formula (1) is not modified.

[Purification Method by Washing with Acidic Aqueous Solution]

Examples of the purification method of the compound represented by the formula (1) by washing with an acidic aqueous solution include, but not particularly limited to, a method described below.

The compound represented by the formula (1) can be purified by a method including a step of first dissolving the compound represented by the formula (1) in an organic solvent optionally immiscible with water, next bringing the solution into contact with an acidic aqueous solution for performing an extraction treatment, to thereby transfer a metal content included in the solution (B) including the compound and the organic solvent to an aqueous phase, and then separating an organic phase and the aqueous phase. The purification tends to allow the contents of various metals in the composition for forming an underlayer film for lithography of the present embodiment to be reduced.

The organic solvent optionally immiscible with water is not particularly limited, but it is preferably an organic solvent that can be safely applied to a semiconductor manufacturing process. The amount of the organic solvent to be used is usually about 1 to 100 times by mass the amount of the compound to be used.

Specific examples of the organic solvent to be used include, but not limited to the following, ethers such as diethyl ether and diisopropyl ether, esters such as ethyl acetate, n-butyl acetate and isoamyl acetate, ketones such as methyl ethyl ketone, methyl isobutyl ketone, ethyl isobutyl ketone, cyclohexanone, cyclopentanone, 2-heptanone and 2-pentanone, glycol ether acetates such as ethylene glycol monoethyl ether acetate, ethylene glycol monobutyl ether acetate, propylene glycol monomethyl ether acetate (PGMEA) and propylene glycol monoethyl ether acetate, aliphatic hydrocarbons such as n-hexane and n-heptane, aromatic hydrocarbons such as toluene and xylene, and halogenated hydrocarbons such as methylene chloride and chloroform. Among them, toluene, 2-heptanone, cyclohexanone, cyclopentanone, methyl isobutyl ketone, propylene glycol monomethyl ether acetate, ethyl acetate, and the like are preferable, and particularly, cyclohexanone and propylene glycol monomethyl ether acetate are preferable. These organic solvents can be used singly or as a mixture of two or more thereof.

The acidic aqueous solution is appropriately selected from aqueous solutions in which an organic or inorganic compound commonly known is dissolved in water. Specific examples of the acidic aqueous solution include, but not limited to the following, an aqueous solution in which a mineral acid such as hydrochloric acid, sulfuric acid, nitric acid or phosphoric acid is dissolved in water, or an aqueous solution in which an organic acid such as acetic acid, propionic acid, oxalic acid, malonic acid, succinic acid, fumaric acid, maleic acid, tartaric acid, citric acid, methanesulfonic acid, phenolsulfonic acid, p-toluenesulfonic acid or trifluoroacetic acid is dissolved in water. These acidic aqueous solutions can be used singly or in combinations of two or more thereof. Among these acidic aqueous solutions, an aqueous solution of sulfuric acid, nitric acid, or a carboxylic acid such as acetic acid, oxalic acid, tartaric acid or citric acid is preferable, an aqueous solution of sulfuric acid, oxalic acid, tartaric acid or citric acid is more preferable, and an aqueous solution of oxalic acid is further preferable. It is considered that a polyvalent carboxylic acid such as oxalic acid, tartaric acid and citric acid is coordinated with a metal ion to exert a chelating effect, and therefore can allow a metal to be more removed. In addition, the water to be here used is preferably water having a low metal content according to the purpose of the present embodiment, and, for example, ion-exchange water is preferable.

The pH of the acidic aqueous solution is not particularly limited, but the acidity of the aqueous solution is preferably adjusted in consideration of the effect on the compound or the resin to be used. The pH is usually in the range from about 0 to 5, preferably about 0 to 3.

The amount of the acidic aqueous solution is not particularly limited, but the amount to be used is preferably adjusted from the viewpoint of reducing the number of extractions for metal removal and the viewpoint of ensuring operation property in consideration of the total amount of the liquid. The amount of the aqueous solution to be used is usually 10 to 200% by mass, preferably 20 to 100% by mass, based on the solution of the compound or the resin to be used.

The solution (B) including the compound represented by the formula (1) and the organic solvent optionally immiscible with water is preferably brought into contact with the acidic aqueous solution to thereby extract the metal content.

The temperature in performing of the extraction treatment is usually in the range from 20 to 90° C., preferably 30 to 80° C. The extraction operation is performed by, for example, well mixing with stirring or the like and thereafter standing. Thus, the metal content included in the solution including the compound to be used and the organic solvent is transferred to the aqueous phase. In addition, the operation tends to allow the acidity of the solution to be reduced, suppressing the change of properties of the compound to be used.

After the extraction treatment, preferably, separation to the solution phase including the compound to be used and the organic solvent, and the aqueous phase is performed and the solution including the organic solvent is recovered by decantation or the like. The standing time is not particularly limited, but the standing time is preferably adjusted from the viewpoint of providing better separation to the solution phase including the organic solvent, and the aqueous phase. The standing time is usually 1 minute or more, preferably 10 minutes or more, more preferably 30 minutes or more. In addition, the extraction treatment may be performed only once, but is also effectively performed with operations such as mixing, standing and separation being repeatedly performed multiple times.

When such an extraction treatment is performed by using the acidic aqueous solution, the solution including the organic solvent extracted and recovered from the aqueous solution after the treatment is preferably further subjected to the extraction treatment with water. Such an extraction operation with water is performed by, for example, well mixing with stirring or the like and thereafter standing. The resulting solution is separated to the solution phase including the compound and the organic solvent, and the aqueous phase, and therefore the solution phase is recovered by decantation or the like. In addition, the water to be here used is preferably water having a low metal content according to the purpose of the present embodiment, such as ion-exchange water. The extraction treatment may be performed only once, but is also effectively performed with operations such as mixing, standing and separation being repeatedly performed multiple times. In addition, conditions in the extraction treatment, such as the ratio of both to be used, the temperature and the time, are not particularly limited, but may be the same as in the case of the contact treatment with the acidic aqueous solution above.

The water content that can be incorporated in the solution thus obtained, including the compound and the organic solvent, can be easily removed by performing an operation such as distillation under reduced pressure. In addition, an organic solvent can be if necessary added to adjust the concentration of the compound to any concentration.

The method of isolating the compound from the resulting solution including the organic solvent is not particularly limited, but it can be performed by a known method such as removal under reduced pressure, separation by reprecipitation and a combination thereof. If necessary, a known treatment such as a concentration operation, a filtration operation, a centrifugation operation and a drying operation can be further performed.

[Solvent Component (S)]

As the solvent (solvent component (S)) for use in the composition for forming an underlayer film for lithography of the present embodiment, a known solvent can be appropriately used as long as it dissolves at least the compound represented by the formula (1). Specific examples of the solvent component (S) include ketone-based solvents such as acetone, methyl ethyl ketone, methyl isobutyl ketone and cyclohexanone; cellosolve-based solvents such as propylene glycol monomethyl ether and propylene glycol monomethyl ether acetate; ester-based solvents such as ethyl lactate, methyl acetate, ethyl acetate, butyl acetate, isoamyl acetate, ethyl lactate, methyl methoxypropionate and methyl hydroxyisobutyrate; alcohol-based solvents such as methanol, ethanol, isopropanol and 1-ethoxy-2-propanol; and aromatic hydrocarbons such as toluene, xylene and anisole, but are not particularly limited thereto. These solvents can be used singly or in combinations of two or more thereof.

Among the solvents, preferable are cyclohexanone, propylene glycol monomethyl ether, propylene glycol monomethyl ether acetate, ethyl lactate, methyl hydroxyisobutyrate, and anisole, in terms of safety.

The content of the solvent component (S) is not particularly limited, but it is preferably 25 to 9,900 parts by mass, more preferably 150 to 4,900 parts by mass, further preferably 400 to 4,900 parts by mass, based on 100 parts by mass of the component (A) (namely, component including the compound represented by the formula (1)) other than the solvent component (S), in terms of solubility and film formation.

[Crosslinking Agent, Acid Generating Agent, and Other Component]

The composition for forming an underlayer film for lithography of the present embodiment may contain, if necessary, a crosslinking agent, an acid generating agent and other component, other than the compound represented by the formula (1) and the solvent component (S). Hereinafter, these optional components will be described.

In the composition for forming an underlayer film for lithography of the present embodiment, the component (A) preferably contains a crosslinking agent from the viewpoint of suppression of intermixing, and the like. Specific examples of the crosslinking agent usable in the present embodiment include a melamine compound, a guanamine compound, a glycoluril compound, a urea compound, an epoxy compound, a thioepoxy compound, an isocyanate compound, an azide compound, and a compound including a double bond such as an alkenyl ether group, these compounds being substituted with at least one group selected from a methylol group, an alkoxymethyl group and an acyloxymethyl group, as a substituent (crosslinkable group), but are not particularly limited thereto. Herein, these crosslinking agents can be used singly or in combinations of two or more thereof. Such a crosslinking agent can also be used as an additive. Herein, the crosslinkable group may also be introduced as a pendant group into the compound represented by the formula (1). A compound including a hydroxy group can also be used as the crosslinking agent.

Specific examples of the melamine compound include, but are not limited to the following, hexamethylolmelamine, hexamethoxymethylmelamine, a compound in which 1 to 6 methylol groups in hexamethylolmelamine are methoxymethylated, or mixtures thereof, and hexamethoxyethylmelamine, hexaacyloxymethylmelamine, a compound in which 1 to 6 methylol groups in hexamethylolmelamine are acyloxymethylated, or mixtures thereof. Specific examples of the epoxy compound include, but are not limited to the following, tris(2,3-epoxypropyl)isocyanurate, trimethylolmethane triglycidyl ether, trimethylolpropane triglycidyl ether, and triethylolethane triglycidyl ether.

Specific examples of the guanamine compound include, but are not limited to the following, tetramethylolguanamine, tetramethoxymethylguanamine, a compound in which 1 to 4 methylol groups in tetramethylolguanamine are methoxymethylated, or mixtures thereof, and tetramethoxyethylguanamine, tetraacyloxyguanamine, a compound in which 1 to 4 methylol groups in tetramethylolguanamine are acyloxymethylated, or mixtures thereof. Specific examples of the glycoluril compound include, but are not limited to the following, tetramethylolglycoluril, tetramethoxyglycoluril, tetramethoxymethylglycoluril, a compound in which 1 to 4 methylol groups in tetramethylolglycoluril are methoxymethylated, or mixtures thereof, and a compound in which 1 to 4 methylol groups in tetramethylolglycoluril are acyloxymethylated, or mixtures thereof. Specific examples of the urea compound include, but are not limited to the following, tetramethylolurea, tetramethoxymethylurea, a compound in which 1 to 4 methylol groups in tetramethylolurea are methoxymethylated, or mixtures thereof, and tetramethoxyethylurea.

Specific examples of the compound including an alkenyl ether group include, but are not limited to the following, ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylolpropane trivinyl ether.

In the composition for forming an underlayer film for lithography according to the present embodiment, the content of the crosslinking agent is not particularly limited, but the content is preferably 0 to 50 parts by mass and more preferably 0 to 40 parts by mass, based on 100 parts by mass of the compound represented by the formula (1). The content is set within the above preferable range to result in tendencies to suppress the occurrence of the mixing phenomenon with the resist layer, and to result in tendencies to enhance an antireflective effect and improve film formability after crosslinking.

In the composition for forming an underlayer film for lithography of the present embodiment, the component (A) preferably contains an acid generating agent from the viewpoint of further promoting a crosslinking reaction by heat. As the acid generating agent, one for generating an acid by pyrolysis and one for generating an acid by light irradiation are known, and any of them can be used.

The acid generating agent includes:
1) an onium salt of the following general formula (P1a-1), (P1a-2), (P1a-3) or (P1b),
2) a diazomethane derivative of the following general formula (P2),
3) a glyoxime derivative of the following general formula (P3),
4) a bissulfone derivative of the following general formula (P4),
5) a sulfonic acid ester of an N-hydroxyimide compound of the following general formula (P5),
6) a β-ketosulfonic acid derivative,
7) a disulfone derivative,
8) a nitrobenzylsulfonate derivative, and
9) a sulfonic acid ester derivative, but is not limited thereto.
Herein, these acid generating agents can be used alone, or two or more thereof can be used in combination.

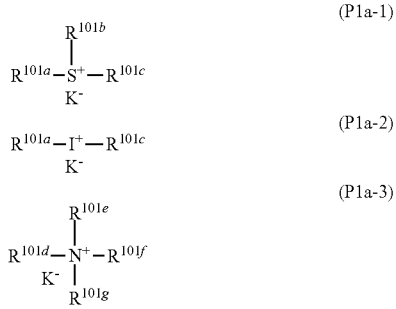

(In the above formulae, each of $R^{101a}$, $R^{101b}$ and $R^{101c}$ independently represents a straight, branched or cyclic alkyl group, alkenyl group, oxoalkyl group or oxoalkenyl group having 1 to 12 carbon atoms; an aryl group having 6 to 20 carbon atoms; or an aralkyl group or aryloxoalkyl group having 7 to 12 carbon atoms, and a part or all of hydrogen atoms of these groups may be substituted with an alkoxy group or the like. In addition, $R^{101b}$ and $R^{101c}$ may form a ring, and if forming a ring, each of $R^{101b}$ and $R^{101c}$ independently represents an alkylene group having 1 to 6 carbon atoms. $K^-$ represents a non-nucleophilic counter ion, $R^{101d}$, $R^{101e}$, $R^{101f}$ and $R^{101g}$ are represented by each independently adding a hydrogen atom to $R^{101a}$, $R^{101b}$ and $R^{101c}$. $R^{101d}$ and $R^{101e}$, and $R^{101d}$, $R^{101e}$ and $R^{101f}$ may form a ring, and if forming a ring, $R^{101d}$ and $R^{101e}$, and $R^{101d}$, $R^{101e}$ and $R^{101f}$ represent an alkylene group having 3 to 10 carbon atoms, or a heteroaromatic ring having therein the nitrogen atom(s) in the formula.)

$R^{101a}$, $R^{101b}$, $R^{101c}$, $R^{101d}$, $R^{101e}$, $R^{101f}$ and $R^{101g}$ described above may be the same or different from one another. Specifically, examples of the alkyl group include, but are not limited to the following, a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cycloheptyl group, a cyclopropylmethyl group, a 4-methyl cyclohexyl group, a cyclohexylmethyl group, a norbornyl group, and an adamantyl group. Examples of the alkenyl group include, but are not limited to the following, a vinyl group, an allyl group, a propenyl group, a butenyl group, a hexenyl group, and a cyclohexenyl group. Examples of the oxoalkyl group can include, but are not limited to the following, a 2-oxocyclopentyl group, a 2-oxocyclohexyl group, a 2-oxopropyl group, a 2-cyclopentyl-2-oxoethyl group, a 2-cyclohexyl-2-oxoethyl group, and a 2-(4-methylcyclohexyl)-2-oxoethyl group. Examples of the oxoalkenyl group include, but are not limited to the following, a 2-oxo-4-cyclohexenyl group and a 2-oxo-4-propenyl group. Examples of the aryl group include, but are not limited to the following, a phenyl group, a naphthyl group, alkoxyphenyl groups such as a p-methoxyphenyl group, a m-methoxyphenyl group, an o-methoxyphenyl group, an ethoxyphenyl group, a p-tert-butoxyphenyl group, and a m-tert-butoxyphenyl group; alkylphenyl groups such as a 2-methylphenyl group, a 3-methylphenyl group, a 4-methylphenyl group, an ethylphenyl group, a 4-tert-butylphenyl group, a 4-butylphenyl group, and a dimethylphenyl group; alkylnaphthyl groups such as a methylnaphthyl group and an ethylnaphthyl group; alkoxynaphthyl groups such as a methoxynaphthyl group and an ethoxynaphthyl group; dialkylnaphthyl groups such as a dimethylnaphthyl group and a diethylnaphthyl group; and dialkoxynaphthyl groups such as a dimethoxynaphthyl group and a diethoxynaphthyl group. Examples of the aralkyl group include, but are not limited to the following, a benzyl group, a phenylethyl group, and a phenethyl group. Examples of the aryloxoalkyl group include, but are not limited to the following, 2-aryl-2-oxoethyl groups such as a 2-phenyl-2-oxoethyl group, a 2-(1-naphthyl)-2-oxoethyl group, and a 2-(2-naphthyl)-2-oxoethyl group. Examples of the non-nucleophilic counter ion, $K^-$, include, but are not limited to the following, halide ions such as a chloride ion and a bromide ion; fluoroalkyl sulfonates such as triflate, 1,1,1-trifluoroethane sulfonate, and nonafluorobutane sulfonate; aryl sulfonates such as tosylate, benzene sulfonate, 4-fluorobenzene sulfonate, and 1,2,3,4,5-pentafluorobenzene sulfonate; and alkyl sulfonates such as mesylate and butane sulfonate.

In the case where $R^{101d}$, $R^{101e}$, $R^{101f}$ and $R^{101g}$ are each a heteroaromatic ring having the nitrogen atom(s) in the formula, examples of the heteroaromatic ring include imidazole derivatives (for example, imidazole, 4-methylimidazole, and 4-methyl-2-phenylimidazole), pyrazole derivatives, furazan derivatives, pyrroline derivatives (for example, pyrroline and 2-methyl-1-pyrroline), pyrrolidine derivatives (for example, pyrrolidine, N-methylpyrrolidine, pyrrolidinone, and N-methylpyrrolidone), imidazoline derivatives, imidazolidine derivatives, pyridine derivatives (for example, pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (for example, quinoline and 3-quinolinecarbonitrile), isoquinoline derivatives, cinnoline derivatives, quinazoline derivatives, quinoxaline derivatives, phthalazine derivatives, purine derivatives, pteridin derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivative, and uridine derivatives.

The onium salts of the formula (P1a-1) and the formula (P1a-2) have functions as a photo acid generating agent and a thermal acid generating agent. The onium salt of the formula (P1a-3) has a function as a thermal acid generating agent.

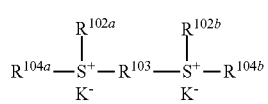
(P1b)

(In the formula (P1b), each of $R^{102a}$ and $R^{102b}$ independently represents a straight, branched or cyclic alkyl group having 1 to 8 carbon atoms. $R^{103}$ represents a straight, branched or cyclic alkylene group having 1 to 10 carbon atoms. Each of $R^{104a}$ and $R^{104b}$ independently represents a 2-oxoalkyl group having 3 to 7 carbon atoms. $K^-$ represents a non-nucleophilic counter ion.)

Specific examples of $R^{102a}$ and $R^{102b}$ include, but are not limited to the following, a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cyclopropylmethyl group, a 4-methyl cyclohexyl group, and a cyclohexylmethyl group. Specific examples of $R^{103}$ include, but are not limited to the following, a methylene group, an ethylene group, a propylene group, a butylene group, a pentylene group, a hexylene group, a heptylene group, an octylene group, a nonylene group, a 1,4-cyclohexylene group, a 1,2-cyclohexylene group, a 1,3-cyclopentylene group, a 1,4-cyclooctylene group, and a 1,4-cyclohexanedimethylene group. Specific examples of $R^{104a}$ and $R^{104b}$ include, but are not limited to the following, a 2-oxopropyl group, a 2-oxocyclopentyl group, a 2-oxocyclohexyl group, and a 2-oxocycloheptyl group. $K^-$ includes the same as those described in the formula (P1a-1), (P1a-2) and (P1a-3).

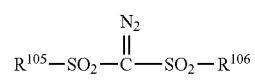
(P2)

In the formula (P2), each of $R^{105}$ and $R^{106}$ independently represents a straight, branched or cyclic alkyl group or halogenated alkyl group having 1 to 12 carbon atoms, an aryl group or halogenated aryl group having 6 to 20 carbon atoms, or an aralkyl group having 7 to 12 carbon atoms.

Examples of the alkyl group in each of $R^{105}$ and $R^{106}$ include, but are not limited to the following, a methyl group, an ethyl group, a propyl group, an isopropyl group, a n-butyl group, a sec-butyl group, a tert-butyl group, a pentyl group, a hexyl group, a heptyl group, an octyl group, an amyl group, a cyclopentyl group, a cyclohexyl group, a cycloheptyl group, a norbornyl group, and an adamantyl group. Examples of the halogenated alkyl group include, but are not limited to the following, a trifluoromethyl group, a 1,1,1-trifluoroethyl group, a 1,1,1-trichloroethyl group, and a nonafluorobutyl group. Examples of the aryl group include, but are not limited to the following, alkoxyphenyl groups such as a phenyl group, a p-methoxyphenyl group, a m-methoxyphenyl group, an o-methoxyphenyl group, an ethoxyphenyl group, a p-tert-butoxyphenyl group, and a m-tert-butoxyphenyl group; and alkylphenyl groups such as a 2-methylphenyl group, a 3-methylphenyl group, a 4-methylphenyl group, an ethylphenyl group, a 4-tert-butylphenyl group, a 4-butylphenyl group, and a dimethylphenyl group. Examples of the halogenated aryl group include, but are not limited to the following, a fluorophenyl group, a chlorophenyl group, and a 1,2,3,4,5-pentafluorophenyl group. Examples of the aralkyl group include, but are not limited to the following, a benzyl group and a phenethyl group.

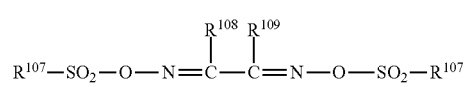
(P3)

In the formula (P3), each of $R^{107}$, $R^{108}$ and $R^{109}$ independently represents a straight, branched or cyclic alkyl group or halogenated alkyl group having 1 to 12 carbon atoms; an aryl group or halogenated aryl group having 6 to 20 carbon atoms; or an aralkyl group having 7 to 12 carbon atoms. $R^{108}$ and $R^{109}$ may be bonded with each other to form a cyclic structure, and if forming a cyclic structure, each of $R^{108}$ and $R^{109}$ represents a straight or branched alkylene group having 1 to 6 carbon atoms.

The alkyl group, halogenated alkyl group, aryl group, halogenated aryl group, and aralkyl group in each of $R^{107}$, $R^{108}$ and $R^{109}$ include the same as those described in $R^{105}$ and $R^{106}$. Herein, examples of the alkylene group in each of $R^{108}$ and $R^{109}$ include, but are not limited to the following, a methylene group, an ethylene group, a propylene group, a butylene group, and a hexylene group.

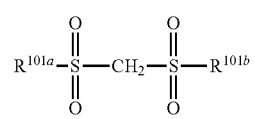
(P4)

In the formula (P4), $R^{101a}$ and $R^{101b}$ are the same as those described above.

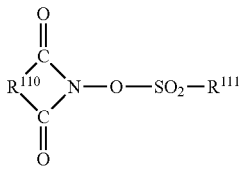
(P5)

In the formula (P5), $R^{110}$ represents an arylene group having 6 to 10 carbon atoms, an alkylene group having 1 to 6 carbon atoms, or an alkenylene group having 2 to 6 carbon atoms, and a part or all of hydrogen atoms of these groups may be further substituted with a straight or branched alkyl group or alkoxy group having 1 to 4 carbon atoms, a nitro group, an acetyl group, or a phenyl group. $R^{111}$ represents a straight, branched or substituted alkyl group, alkenyl group or alkoxyalkyl group having 1 to 8 carbon atoms, a phenyl group, or a naphthyl group. A part or all of hydrogen atoms of these groups may be further substituted with an alkyl group or alkoxy group having 1 to 4 carbon atoms, a nitro group, an acetyl group, or a phenyl group. $R^{111}$ represents a straight, branched or substituted alkyl group, alkenyl group or alkoxyalkyl group having 1 to 8 carbon atoms, a phenyl group, or a naphthyl group. A part or all of hydrogen atoms of these groups may be further substituted with an alkyl group or alkoxy group having 1 to 4 carbon atoms; a phenyl group that may be substituted with an alkyl group or alkoxy group having 1 to 4 carbon atoms, a nitro group or an acetyl group; a heteroaromatic group having 3 to 5 carbon atoms; or a chlorine atom or a fluorine atom.

Herein, examples of the arylene group in $R^{110}$ include, but are not limited to the following, a 1,2-phenylene group and a 1,8-naphthylene group. Examples of the alkylene group include, but are not limited to the following, a methylene group, an ethylene group, a trimethylene group, a tetramethylene group, a phenylethylene group, and a norbornane-2,3-diyl group. Examples of the alkenylene group include, but are not limited to the following, a 1,2-vinylene group, a 1-phenyl-1,2-vinylene group, and a 5-norbornene-2,3-diyl group. The alkyl group in $R^{111}$ includes the same as those in $R^{101a}$ to $R^{101c}$. Examples of the alkenyl group include, but are not limited to the following, a vinyl group, a 1-propenyl group, an allyl group, a 1-butenyl group, a 3-butenyl group, an isoprenyl group, a 1-pentenyl group, a 3-pentenyl group, a 4-pentenyl group, a dimethylallyl group, a 1-hexenyl group, a 3-hexenyl group, a 5-hexenyl group, a 1-heptenyl group, a 3-heptenyl group, a 6-heptenyl group, and a 7-octenyl group. Examples of the alkoxyalkyl group include, but are not limited to the following, a methoxymethyl group, an ethoxymethyl group, a propoxymethyl group, a butoxymethyl group, a pentyloxymethyl group, a hexyloxymethyl group, a heptyloxymethyl group, a methoxyethyl group, an ethoxyethyl group, a propoxyethyl group, a butoxyethyl group, a pentyloxyethyl group, a hexyloxyethyl group, a methoxypropyl group, an ethoxypropyl group, a propoxypropyl group, a butoxypropyl group, a methoxybutyl group, an ethoxybutyl group, a propoxybutyl group, a methoxypentyl group, an ethoxypentyl group, a methoxyhexyl group, and a methoxyheptyl group.

Herein, Examples of the alkyl group having 1 to 4 carbon atoms, which may be further substituted, include, but are not limited to the following, a methyl group, an ethyl group, a propyl group, an isopropyl group, a n-butyl group, a an isobutyl group, and a tert-butyl group. Examples of the alkoxy group having 1 to 4 carbon atoms include, but are not limited to the following, a methoxy group, an ethoxy group, a propoxy group, an isopropoxy group, a n-butoxy group, an isobutoxy group, and tert-butoxy group. Examples of the phenyl group that may be substituted with an alkyl group or alkoxy group having 1 to 4 carbon atoms, a nitro group, or an acetyl group include, but are not limited to the following, a phenyl group, a tolyl group, a p-tert-butoxyphenyl group, a p-acetylphenyl group, and a p-nitrophenyl group. Examples of the heteroaromatic group having 3 to 5 carbon atoms include, but are not limited to the following, a pyridyl group and a furyl group.

Specific examples of the acid generating agent include, but are not limited to the following, onium salts such as tetramethylammonium trifluoromethanesulfonate, tetramethylammonium nonafluorobutanesulfonate, triethylammonium nonafluorobutanesulfonate, pyridinium nonafluorobutanesulfonate, triethylammonium camphorsulfonate, pyridinium camphorsulfonate, tetra n-butylammonium nonafluorobutanesulfonate, tetraphenylammonium nonafluorobutanesulfonate, tetramethylammonium p-toluenesulfonate, diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl) diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, ethylene bis[methyl(2-oxocyclopentyl)sulfonium trifluoromethanesulfonate], and 1,2'-naphthylcarbonylmethyltetrahydrothiophenium triflate; diazomethane derivatives such as bis(benzenesulfonyl)diazomethane, bis(p-toluenesulfonyl)diazomethane, bis(xylenesulfonyl)diazomethane, bis(cyclohexylsulfonyl)diazomethane, bis(cyclopentylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, bis(tert-butylsulfonyl)diazomethane, bis(n-amylsulfonyl)diazomethane, bis(isoamylsulfonyl)diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane, and 1-tert-amylsulfonyl-1-(tert-butylsulfonyl)diazomethane; glyoxime derivatives such as bis-(p-toluenesulfonyl)-α-dimethylglyoxime, bis-(p-toluesulfonyl)-α-diphenylglyoxime, bis-(p-toluenesulfonyl)-α-dicyclohexylglyoxime, bis-(p-toluenesulfonyl)-2,3-pentanedioneglyoxime, bis-(p-toluenesulfonyl)-2-methyl-3,4-pentanedioneglyoxime, bis-(n-butanesulfonyl)-α-dimethylglyoxime, bis-(n-butanesulfonyl)-α-diphenylglyoxime, bis-(n-butanesulfonyl)-α-dicyclohexylglyoxime, bis-(n-butanesulfonyl)-2,3-pentanedioneglyoxime, bis-(n-butanesulfonyl)-2-methyl-3,4-pentanedioneglyoxime, bis-(methanesulfonyl)-α-dimethylglyoxime, bis-(trifluoromethanesulfonyl)-α-dimethylglyoxime, bis-(1,1,1-trifluoroethanesulfonyl)-α-dimethylglyoxime, bis-(tert-butanesulfonyl)-α-dimethylglyoxime, bis-(perfluorooctanesulfonyl)-α-dimethylglyoxime, bis-(cyclohexanesulfonyl)-α-dimethylglyoxime, bis-(benzenesulfonyl)-α-dimethylglyoxime, bis-(p-fluorobenzenesulfonyl)-α-dimethylglyoxime, bis-(p-tert-butylbenzenesulfonyl)-α-dimethylglyoxime, bis-(xylenesulfonyl)-α-dimethylglyoxime, and bis-(camphorsulfonyl)-α-dimethylglyoxime; bissulfone derivatives, such as bisnaphthylsulfonylmethane, bistrifluoromethylsulfonylmethane, bismethylsulfonylmethane, bisethylsulfonylmethane, bispropylsulfonylmethane, bisisopropylsulfonylmethane, bis-p-toluenesulfonylmethane, and bisbenzenesulfonylmethane; β-ketosulfone derivatives such as 2-cyclohexylcarbonyl-2-(p-toluenesulfonyl)propane and 2-isopropylcarbonyl-2-(p-toluenesulfonyl)propane; disulfone derivatives such as a diphenyldisulfone derivative and a dicyclohexyldisulfone derivative, nitrobenzylsulfonate derivatives such as 2,6-dinitrobenzyl p-toluenesulfonate and 2,4-dinitrobenzyl p-toluenesulfonate; sulfonic acid ester derivatives such as 1,2,3-tris(methanesulfonyloxy)benzene, 1,2,3-tris(trifluoromethanesulfonyloxy)benzene, and 1,2,3-tris(p-toluenesulfonyloxy)benzene; and sulfonic acid ester derivatives of a N-hydroxyimide compound, such as N-hydroxysuccinimide methanesulfonic acid ester, N-hydroxysuccinimide trifluoromethanesulfonic acid ester, N-hydroxysuccinimide ethanesulfonic acid ester, N-hydroxysuccinimide 1-propanesulfonic acid ester, N-hydroxysuccinimide 2-propanesulfonic acid ester, N-hydroxysuccinimide 1-pentanesulfonic acid ester, N-hydroxysuccinimide 1-octanesulfonic acid ester, N-hydroxysuccinimide p-toluenesulfonic acid ester, N-hydroxysuccinimide p-methoxybenzenesulfonic acid ester, N-hydroxysuccinimide 2-chloroethanesulfonic acid ester, N-hydroxysuccinimide benzenesulfonic acid ester, N-hydroxysuccinimide-2,4,6-trimethylbenzenesulfonic acid ester, N-hydroxysuccinimide 1-naphthalenesulfonic acid ester, N-hydroxysuccinimide 2-naphthalenesulfonic acid ester, N-hydroxy-2-phenylsuccinimide methanesulfonic acid ester, N-hydroxymaleimide methanesulfonic acid ester, N-hydroxymaleimide ethanesulfonic acid ester, N-hydroxy-2-phenylmaleimide methanesulfonic acid ester, N-hydroxyglutarimide methanesulfonic acid ester, N-hydroxyglutarimide benzenesulfonic acid ester, N-hydroxyphthalimide methanesulfonic acid ester, N-hydroxyphthalimide benzenesulfonic acid ester, N-hydroxyphthalimide trifluoromethanesulfonic acid ester, N-hydroxyphthalimide p-toluenesulfonic acid ester, N-hydroxynaphthalimide methanesulfonic acid ester, N-hydroxynaphthalimide benzenesulfonic acid ester, N-hydroxy-5-norbornene-2,3-dicarboxyimide methanesulfonic acid ester, N-hydroxy-5-norbornene-2,3-dicarboxyimide trifluoromethanesulfonic acid ester, and N-hydroxy-5-norbornene-2,3-dicarboxyimide p-toluenesulfonic acid ester.

Among them, in particular, onium salts such as triphenylsulfonium trifluoromethanesulfonate, (p-tert-butoxyphenyl) diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbornyl) methyl(2-oxocyclohexyl)sulfonium trifluoromethanesulfonate, and 1,2'-naphthylcarbonylmethyltetrahydrothiophenium triflate; diazomethane derivatives such as bis(benzenesulfonyl)diazomethane, bis(p-toluenesulfonyl)diazomethane, bis(cyclohexylsulfonyl)diazomethane, bis(n-butylsulfonyl)diazomethane, bis(isobutylsulfonyl)diazomethane, bis(sec-butylsulfonyl)diazomethane, bis(n-propylsulfonyl) diazomethane, bis(isopropylsulfonyl)diazomethane, and bis(tert-butylsulfonyl)diazomethane; glyoxime derivatives such as bis-(p-toluenesulfonyl)-α-dimethylglyoxime and bis-(n-butanesulfonyl)-α-dimethylglyoxime, bissulfone derivatives such as bisnaphthylsulfonylmethane; and sulfonic acid ester derivatives of an N-hydroxyimide compound, such as N-hydroxysuccinimide methanesulfonic acid ester, N-hydroxysuccinimide trifluoromethanesulfonic acid ester, N-hydroxysuccinimide 1-propanesulfonic acid ester, N-hydroxysuccinimide 2-propanesulfonic acid ester, N-hydroxysuccinimide 1-pentanesulfonic acid ester, N-hydroxysuccinimide p-toluenesulfonic acid ester, N-hydroxynaphthalimide methanesulfonic acid ester, and N-hydroxynaphthalimide benzenesulfonic acid ester, and the like are preferably used.

In the composition for forming an underlayer film for lithography of the present embodiment, the content of the acid generating agent is not particularly limited, but the content is preferably 0 to 50 parts by mass, more preferably 0 to 40 parts by mass, based on 100 parts by mass of the compound represented by the formula (1). The content is set within the above preferable range to result in tendency to promote a crosslinking reaction, and also to result in a tendency to suppress the occurrence of the mixing phenomenon with a resist layer.

Furthermore, in the composition for forming an underlayer film for lithography of the present embodiment, the component (A) preferably contains a basic compound from the viewpoint of improving preservation stability.

The basic compound serves as a quencher to an acid for preventing a trace amount of the acid generated from the acid generating agent from promoting a crosslinking reaction. Examples of such a basic compound include primary, secondary, and tertiary aliphatic amines, mixed amines, aromatic amines, heterocyclic amines, a nitrogen-containing compound having a carboxy group, a nitrogen-containing compound having a sulfonyl group, a nitrogen-containing compound having a hydroxyl group, a nitrogen-containing compound having a hydroxyphenyl group, an alcoholic nitrogen-containing compound, an amide derivative, and an imide derivative, but are not limited thereto.

Specifically, specific examples of the primary aliphatic amines include, but are not limited to the following, ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Specific examples of the secondary aliphatic amines include, but are not limited to the following, dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Specific examples of the tertiary aliphatic amines include, but are not limited to the following, trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Specific examples of the mixed amines include, but are not limited to the following, dimethylethylamine, methylethylpropylamine, benzylamine, phenethylamine, and benzyldimethylamine. Specific examples of the aromatic amines and heterocyclic amines include, but are not limited to the following, aniline derivatives (for example, aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (for example, pyrrole, 2H-pyrrole, 1-methylpyrrole, 2,4-dimethylpyrrole, 2,5-dimethylpyrrole, and N-methylpyrrole), oxazole derivatives (for example, oxazole and isoxazole), thiazole derivatives (for example, thiazole and isothiazole), imidazole derivatives (for example, imidazole, 4-methylimidazole, and 4-methyl-2-phenylimidazole), pyrazole derivatives, furazan derivatives, pyrroline derivatives (for example, pyrroline and 2-methyl-1-pyrroline), pyrrolidine derivatives (for example, pyrrolidine, N-methylpyrrolidine, pyrrolidinone, and N-methylpyrrolidone), imidazoline derivatives, imidazolidine derivatives, pyridine derivatives (for example, pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (for example, quinoline, 3-quinolinecarbonitrile), isoquinoline derivatives, cinnoline derivatives, quinazoline derivatives, quinoxaline derivatives, phthalazine derivatives, purine derivatives, pteridin derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Furthermore, specific examples of the nitrogen-containing compound having a carboxy group include, but are not limited to the following, aminobenzoic acid, indolecarboxylic acid, and amino acid derivatives (for example, nicotinic acid, alanine, arginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Specific examples of the nitrogen-containing compound having a sulfonyl group include, but are not limited to the following, 3-pyridinesulfonic acid and pyridinium p-toluenesulfonate. Specific examples of the nitrogen-containing compound having a hydroxyl group, the nitrogen-containing compound having a hydroxyphenyl group, and the alcoholic nitrogen-containing compound include, but are not limited to the following, 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Specific examples of the amide derivative include, but are not limited to the following, formamide, N-methylformamide, N,N-dimethylformamide, acetamide, N-methylacetamide, N,N-dimethylacetamide, propionamide, and benzamide. Specific examples of the imide derivative include, but are not limited to the following, phthalimide, succinimide, and maleimide.

In the composition for forming an underlayer film for lithography according to the present embodiment, the content of the basic compound is not particularly limited, but the content is preferably 0 to 2 parts by mass, more preferably 0 to 1 parts by mass, based on 100 parts by mass of the compound represented by the formula (1). The content is set within the above preferable range to result in a tendency to improve preservation stability without excessively interrupting a crosslinking reaction.

In addition, the composition for forming an underlayer film for lithography of the present embodiment may contain other resins and/or compounds for the purpose of imparting heat curability and controlling absorbance. Such other resins and/or compounds include naphthol resins, xylene resins, naphthol-modified resins, phenol-modified resins of naphthalene resins, polyhydroxystyrene, dicyclopentadiene resins, (meth)acrylate, dimethacrylate, trimethacrylate, tetramethacrylate, resins having a naphthalene ring such as vinylnaphthalene and polyacenaphthylene, resins having a biphenyl ring such as phenanthrenequinone and fluorene, resins having a heterocyclic ring having a hetero atom such as thiophene and indene, and resins not containing an aromatic ring; rosin-based resins, and resins or compounds including an alicyclic structure, such as cyclodextrin, adamantane(poly)ol, tricyclodecane(poly)ol and derivatives thereof, but are not particularly limited thereto. Furthermore, the composition for forming an underlayer film for lithography of the present embodiment can also contain a known additive. Examples of the known additive includes, but not limited to the following, an ultraviolet absorber, a surfactant, a colorant and a non-ionic surfactant.

[Forming Method of Underlayer Film for Lithography and Pattern]

An underlayer film for lithography of the present embodiment is formed by using the composition for forming an underlayer film for lithography of the present embodiment.

In addition, a resist pattern forming method of the present embodiment includes step (A-1) of forming an underlayer film on a substrate by using the composition for forming an underlayer film for lithography of the present embodiment, step (A-2) of forming at least one photoresist layer on the underlayer film, and step (A-3) of, after the second forming step, irradiating a predetermined region of the photoresist layer with radiation, followed by developing.

Furthermore, a circuit pattern forming method of the present embodiment includes step (B-1) of forming an underlayer film on a substrate by using the composition for forming an underlayer film for lithography of the present embodiment, step (B-2) of forming an intermediate layer film on the underlayer film by using a silicon atom-containing resist intermediate layer film material, step (B-3) of forming at least one photoresist layer on the intermediate layer film, step (B-4) of, after step (B-3), irradiating a predetermined region of the photoresist layer with radiation, followed by developing to form a resist pattern, and step (B-5) of, after step (B-4), etching the intermediate layer film with the resist pattern as a mask, etching the underlayer film with the obtained intermediate layer film pattern as an etching mask and etching the substrate with the obtained underlayer film pattern as an etching mask, to form a pattern on the substrate.

The underlayer film for lithography of the present embodiment is not particularly limited in terms of the forming method thereof as long as it is formed from the composition for forming an underlayer film for lithography of the present embodiment, and a known method can be applied. For example, the underlayer film can be formed by applying the composition for forming an underlayer film for lithography of the present embodiment on the substrate by a known coating method or printing method such as spin coating or screen printing, and removing an organic solvent by volatilization or the like.

The underlayer film is preferably baked upon forming in order to suppress the occurrence of the mixing phenomenon with an upperlayer resist and also promote a crosslinking reaction. In this case, the baking temperature is not particularly limited, but it is preferably within the range of 80 to 450° C., and more preferably 200 to 400° C. In addition, the baking time is not also particularly limited, but is preferably within the range of 10 to 300 seconds. Herein, the thickness of the underlayer film can be appropriately selected depending on the required properties, and is not particularly limited, but the thickness is usually preferably about 30 to 20,000 nm and more preferably 50 to 15,000 nm.

After the underlayer film is prepared on the substrate, preferably, in the case of a two-layer process, a silicon-containing resist layer or a usual single-layer resist including a hydrocarbon is prepared on the film for lithography, and in the case of a three-layer process, a silicon-containing intermediate layer is prepared on the film for lithography and a single-layer resist layer not containing silicon is further prepared on the silicon-containing intermediate layer. In these cases, a photoresist material for forming the resist layer, which can be used, is a known one.

As the silicon-containing resist material for a two-layer process, a positive-type photoresist material is preferably used, which contains a silicon atom-containing polymer such as a polysilsesquioxane derivative or a vinylsilane derivative used as a base polymer in the viewpoint of oxygen gas-etching resistance, and an organic solvent, an acid generating agent and if necessary a basic compound. Herein, as the silicon atom-containing polymer, a known polymer used in such a resist material can be used.

As the silicon-containing intermediate layer for a three-layer process, a polysilsesquioxane-based intermediate layer is preferably used. The intermediate layer is allowed to have an effect as an antireflective film, and thus tends to make it possible to effectively suppress reflection. For example, if a material including many aromatic groups and having a high substrate-etching resistance is used for the underlayer film in a 193 nm exposure process, a k-value tends to be increased to increase substrate reflection, but the reflection can be suppressed by the intermediate layer to thereby make the substrate reflection 0.5% or less. For the intermediate layer having such an antireflection effect, but not limited to the following, polysilsesquioxane into which a phenyl group or a light-absorbing group having a silicon-silicon bond for 193 nm exposure is introduced and which is to be crosslinked with an acid or heat is preferably used.

An intermediate layer formed by the Chemical Vapour Deposition (CVD) method can also be used. As the intermediate layer having a high effect as an antireflective film, prepared by the CVD method, but not limited to the following, for example, a SiON film is known. In general, the intermediate layer is formed by a wet process such as a spin coating method or screen printing rather than the CVD method in terms of simplicity and cost effectiveness. Herein, the upperlayer resist in a three-layer process may be of positive-type or negative-type, and the same one as a commonly used single-layer resist can be used therefor.

Furthermore, the underlayer film of the present embodiment can also be used as a usual antireflective film for use in a single-layer resist or a usual underlying material for suppressing pattern collapse. The underlayer film of the present embodiment can also be expected to serve as a hard mask for underlying processing because of being excellent in etching resistance for underlying processing.

In the case where a resist layer is formed by the photoresist material, a wet process such as a spin coating method or screen printing is preferably used as in the case of forming the underlayer film. The resist material is coated by a spin coating method or the like and then usually pre-baked, and such pre-baking is preferably performed in the range of 80 to 180° C. for 10 to 300 seconds. Thereafter, in accordance with an ordinary method, the resultant can be subjected to exposure, post-exposure bake (PEB), and development to obtain a resist pattern. Herein, the thickness of the resist film is not particularly limited, but generally, it is preferably 30 to 500 nm and more preferably 50 to 400 nm.

Light for use in exposure may be appropriately selected depending on the photoresist material to be used. In general, examples thereof include high energy radiation having a wavelength of 300 nm or less, specifically, excimer lasers of 248 nm, 193 nm, and 157 nm, a soft X-ray of 3 to 20 nm, electron beam, and an X-ray.

The resist pattern formed by the above method is a pattern whose collapse is suppressed by the underlayer film of the present embodiment. Therefore, the underlayer film of the present embodiment can be used to thereby obtain a finer pattern, and an exposure amount necessary for obtaining such a resist pattern can be reduced.

Then, the obtained resist pattern is used as a mask to perform etching. As the etching of the underlayer film in a two-layer process, gas etching is preferably used. As the gas etching, etching using oxygen gas is suitable. In addition to oxygen gas, an inert gas such as He and Ar, and CO, $CO_2$, $NH_3$, $SO_2$, $N_2$, $NO_2$, and $H_2$ gases can also be added. The gas etching can also be performed not using oxygen gas but using only CO, $CO_2$, $NH_3$, $N_2$, $NO_2$, and $H_2$ gases. In particular, the latter gases are preferably used for protecting a side wall for preventing a pattern side wall from being undercut.

On the other hand, also in the etching of the intermediate layer in a three-layer process, gas etching is preferably used. As the gas etching, the same one as the one described in a two-layer process can be applied. In particular, the intermediate layer is preferably processed in a three-layer process using a fluorocarbon gas with the resist pattern as a mask. Thereafter, as described above, the intermediate layer pattern is used as a mask to perform, for example, oxygen gas etching, thereby processing the underlayer film.

Herein, in the case where an inorganic hard mask intermediate layer film is formed as the intermediate layer, a silicon oxide film, a silicon nitride film, and a silicon oxynitride film (SiON film) are formed by the CVD method, the ALD method, and the like. The nitride film forming method that can be used is, but not limited to the following, any method described in, for example, Japanese Patent Laid-Open No. 2002-334869 (Patent Literature 6) and WO2004/066377 (Patent Literature 7). While the photoresist film can be directly formed on such an intermediate layer film, an organic antireflective film (BARC) may also be formed on the intermediate layer film by spin coating, and the photoresist film may also be formed thereon.

As the intermediate layer, a polysilsesquioxane-based intermediate layer is also preferably used. The resist intermediate layer film is allowed to have an effect as an antireflective film, and thus tends to make it possible to effectively suppress reflection. A specific material for the polysilsesquioxane-based intermediate layer that can be used is, but not limited to the following, any material described in, for example, Japanese Patent Laid-Open No. 2007-226170 (Patent Literature 8) and Japanese Patent Laid-Open No. 2007-226204 (Patent Literature 9).

The next etching of the substrate can also be performed by an ordinary method, and, for example, when the substrate is made of $SiO_2$ or SiN, etching with mainly a fluorocarbon gas can be performed, and when the substrate is made of p-Si, Al, or W, etching mainly using a chlorine-based gas or bromine-based gas can be performed. In the case where the substrate is processed by the etching with a fluorocarbon gas, the silicon-containing resist in a two-layer resist process and the silicon-containing intermediate layer in a three-layer process are peeled off at the same time as the processing of the substrate. On the other hand, in the case where the substrate is processed by the etching with a chlorine-based gas or bromine-based gas, the silicon-containing resist layer or the silicon-containing intermediate layer is peeled off separately, and is generally peeled off by dry etching with a fluorocarbon gas after the substrate is processed.

The underlayer film of the present embodiment is characterized by being excellent in etching resistance of such a substrate. Herein, the substrate that can be used is appropriately selected from known ones, and is not particularly limited, but includes Si, α-Si, p-Si, $SiO_2$, SiN, SiON, W, TiN, and Al substrates. In addition, the substrate may also be a laminate having a processed film (processed substrate) on a base material (support). Such a processed film includes various Low-k films made of Si, $SiO_2$, SiON, SiN, p-Si, α-Si, W, W—Si, Al, Cu, and Al—Si, and stopper films thereof, and a material different from the base material (support) is usually used therefor. Herein, the thickness of the substrate to be processed or the processed film is not particularly limited, but it is usually preferably about 50 to 10,000 nm and more preferably 75 to 5,000 nm.

EXAMPLES

Hereinafter, the present embodiment will be described by Synthesis Examples and Examples in more detail, but the present embodiment is not limited thereto at all.

[Carbon Concentration and Oxygen Concentration]

The carbon concentration and the oxygen concentration (% by mass) were measured by organic element analysis.

Apparatus: CHN CORDER MT-6 (manufactured by Yanaco Bunseki Kogyo Co.)

[Molecular Weight]

Measurement was performed by LC-MS analysis using Acquity UPLC/MALDI-Synapt HDMS manufactured by Water.

[Molecular Weight in Terms of Polystyrene]

Gel permeation chromatography (GPC) analysis was used to determine the weight average molecular weight (Mw) and the number average molecular weight (Mn) in terms of polystyrene, and to determine the degree of dispersion (Mw/Mn).

Apparatus: Shodex GPC-101 type (manufactured by Showa Denko K. K.)

Column: KF-80M×3

Eluent: THF 1 mL/min

Temperature: 40° C.

[Pyrolysis Temperature (Tg)]

An EXSTAR 6000 TG-DTA apparatus manufactured by SII NanoTechnology Inc. was used, and about 5 mg of a sample was placed in an unsealed aluminum container and heated to 500° C. at a rate of temperature rise of 10° C./min in a nitrogen gas (30 mL/min) stream. In this time, a temperature at which a reducing portion appeared on the base line was defined as a pyrolysis temperature (Tg).

[Solubility]

The amount of the compound dissolved in propylene glycol monomethyl ether acetate (PGMEA) was measured at 23° C., and the results were evaluated according to the following criteria.

Evaluation A: 10% by mass or more

Evaluation B: less than 10% by mass

Synthesis Example 1

Synthesis of 1-Naphthol Aralkyl-based Cyanic Acid Ester Compound (Hereinafter, Abbreviated as "SNCN".)

In 1800 g of dichloromethane were dissolved 300 g (1.28 mol in terms of hydroxy group) of a 1-naphthol aralkyl resin (produced by Nippon Steel & Sumikin Chemical Co., Ltd.) and 194.6 g (1.92 mol) (1.5 mol based on 1 mol of hydroxy group) of triethylamine, to provide solution 1.

Mixed were 125.9 g (2.05 mol) (1.6 mol based on 1 mol of hydroxy group) of cyanogen chloride, 293.8 g of dichloromethane, 194.5 g (1.92 mol) (1.5 mol based on 1 mol of hydroxy group) of 36% hydrochloric acid and 1205.9 g of water, and solution 1 was injected to the mixed liquid over 30 minutes while the mixed liquid was kept at a liquid temperature of −2 to −0.5° C. with stirring. After completion of injection of solution 1, the resultant was stirred at that temperature for 30 minutes, and thereafter a solution (solution 2) in which 65 g (0.64 mol) (0.5 mol based on 1 mol of hydroxy group) of triethylamine was dissolved in 65 g of dichloromethane was injected thereto over 10 minutes. After completion of injection of solution 2, the resultant was stirred at that temperature for 30 minutes to complete the reaction.

Thereafter, the reaction solution was left to still stand to separate an organic phase and an aqueous phase. The resulting organic phase was washed with 1300 g of water five times. The electrical conductivity of the water discharged at the fifth washing with water was 5 μS/cm, and it was thus confirmed that a predetermined ionic compound was sufficiently removed by washing with water. The organic phase after washing with water was concentrated under reduced pressure, and finally concentrated to dryness at 90° C. for 1 hour, to provide 331 g of a cyanic acid ester compound SNCN (orange viscous matter) represented by formula (9).

With respect to the resulting cyanic acid ester compound SNCN, Mn was 350, Mw was 600 and Mw/Mn was 1.71. In addition, the carbon concentration was 82.2% by mass, the oxygen concentration was 7.1% by mass and the nitrogen concentration was 5.3% by mass. The IR spectrum of the SNCN exhibited an absorption at 2250 cm$^{-1}$ (cyanic acid ester group) and no absorption of a hydroxy group.

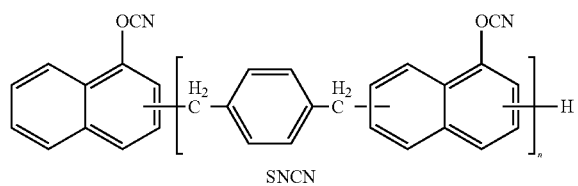

(9)

SNCN

As a result of thermogravimetric measurement (TG), the 10% thermal weight loss temperature of the resulting compound (SNCN) was 400° C. or higher. Therefore, the compound was evaluated to have a high heat resistance and be applicable to high-temperature baking.

As a result of evaluation of the solubility in PGMEA, the solubility was 10% by mass or more (Evaluation A) and compound (SNCN) was evaluated to have an excellent solubility. Therefore, compound (SNCN) was evaluated to have a high storage stability in a solution state and also be sufficiently applicable to an edge bead rinse liquid (mixed liquid of PGME/PGMEA) widely used in a semiconductor microfabrication process.

Production Example 1

A four-neck flask having a bottom outlet and an inner volume of 10 L, equipped with a Dimroth condenser, a thermometer and a stirring blade was prepared. To this four-neck flask were charged 1.09 kg (7 mol, produced by Mitsubishi Gas Chemical Company, Inc.) of 1,5-dimethylnaphthalene, 2.1 kg (28 mol as formaldehyde, produced by Mitsubishi Gas Chemical Company, Inc.) of a 40% by mass aqueous formalin solution and 0.97 mL of 98% by mass sulfuric acid (produced by Kanto Chemical Co., Inc.) under a nitrogen stream, and allowed the reaction to run under normal pressure for 7 hours with refluxing at 100° C. Thereafter, ethylbenzene (special grade chemical, produced by Wako Pure Chemical Industries, Ltd.) (1.8 kg) as a dilution solvent was added to the reaction solution and left to stand, and then an aqueous phase being a bottom phase was removed. Furthermore, the resultant was neutralized and washed with water, and ethylbenzene and the unreacted 1,5-dimethylnaphthalene were distilled off under reduced pressure, thereby providing 1.25 kg of a dimethylnaphthalene formaldehyde resin as a light-brown solid.

With respect to the molecular weight of the resulting dimethylnaphthalene formaldehyde resin, Mn was 562, Mw was 1168 and Mw/Mn was 2.08. In addition, the carbon concentration was 84.2% by mass, and the oxygen concentration was 8.3% by mass.

Subsequently, a four-neck flask having an inner volume of 0.5 L, equipped with a Dimroth condenser, a thermometer and a stirring blade, was prepared. To this four-neck flask were charged 100 g (0.51 mol) of the dimethylnaphthalene formaldehyde resin obtained as described above and 0.05 g of paratoluenesulfonic acid under a nitrogen stream, heated for 2 hours with the temperature being raised to 190° C., and then stirred. Thereafter, 52.0 g (0.36 mol) of 1-naphthol was further added thereto, and further heated to 220° C. to allow the reaction to run for 2 hours. After being diluted with a solvent, the resultant was neutralized and washed with water, and the solvent was removed under reduced pressure to thereby provide 126.1 g of a modified resin (CR-1) as a blackish brown solid.

With respect to the resulting modified resin (CR-1), Mn was 885, Mw was 2220 and Mw/Mn was 4.17. In addition, the carbon concentration was 89.1% by mass and the oxygen concentration was 4.5% by mass.

Examples 1 to 5 and Comparative Example 3

A material for forming an underlayer film for lithography in each of Examples 1 to 5 and Comparative Examples 1 to 2 was prepared using the compound obtained in Synthesis Example 1 above, the resin obtained in Production Example 1 above, and the following materials so that each composition shown in Table 1 was achieved. Herein, each numerical value in Table 1 is expressed by parts by mass under assumption of the amount of the entire material for forming an underlayer film for lithography being 100 parts by mass.

Acid generating agent: di-tert-butyldiphenyliodonium nonafluoromethanesulfonate (DTDPI) produced by Midori Kagaku Co., Ltd.

Crosslinking agent: Nikalac MX270 (Nikalac) produced by Sanwa Chemical Co., Ltd.

Organic solvent: propylene glycol monomethyl ether acetate (PGMEA)

Then, each composition for forming an underlayer film for lithography of Examples 1 to 5 and Comparative Examples 1 to 2 was spin-coated on a silicon substrate, thereafter baked at 180° C. for 60 seconds and further at 400° C. for 120 seconds to prepare each underlayer film having a film thickness of 200 nm. Then, the etching resistance and the heat weight loss were evaluated under conditions shown below. The evaluation results are shown in Table 1.

[Etching Test]
Etching apparatus: RIE-10NR manufactured by Samco Inc.
Output: 50 W
Pressure: 4 Pa
Time: 2 min
Etching gas
CF$_4$ gas flow rate: O$_2$ gas flow rate=5:15 (sccm)
[Evaluation of Etching Resistance]
The evaluation of etching resistance was performed according to the following procedure.

First, an underlayer film of novolac was prepared under the same conditions as those in Example 1 except that novolac (PSM4357 produced by Gunei Chemical Industry Co., Ltd.) was used instead of the compound (SNCN) in Example 1 and the drying temperature was changed to 110° C. Then, the etching test was performed with respect to the underlayer film of novolac as a subject, and the etching rate in that time was measured.

Then, the etching test was performed with respect to each underlayer film of Examples 1 to 5 and Comparative Examples 1 to 2 as a subject, and the etching rate in that time was measured.

Then, the etching resistances were evaluated according to the following criteria based on the etching rate of the underlayer film of novolac. Evaluation A or B is preferable in terms of practical use.

<Evaluation Criteria>

A; etching rate of less than −20% compared with the underlayer film of novolac

B; etching rate of −20% to 0% compared with underlayer film of novolac

C; etching rate of more than 0% compared with the underlayer film of novolac

[Heat Weight Loss]

An EXSTAR 6000 TG-DTA apparatus manufactured by SII NanoTechnology Inc. was used, and about 5 mg of a sample was placed in an unsealed aluminum container and heated to 500° C. at a rate of temperature rise of 10° C./min in a nitrogen gas (30 mL/min) stream. Evaluation A or B is preferable in terms of practical use.

<Evaluation Criteria>

A: heat weight loss at 400° C. of less than 5%
B: heat weight loss at 400° C. of 5% to 25%
C: heat weight loss at 400° C. of more than 25% was subjected to polymerization under a nitrogen atmosphere for 22 hours with the reaction temperature being kept at 63° C., and thereafter the reaction solution was dropped in 400 mL of n-hexane. A product resin thus obtained was solidified and purified, and a white powder produced was taken by filtration and dried under reduced pressure at 40° C. overnight to provide a compound represented by the following formula (10).

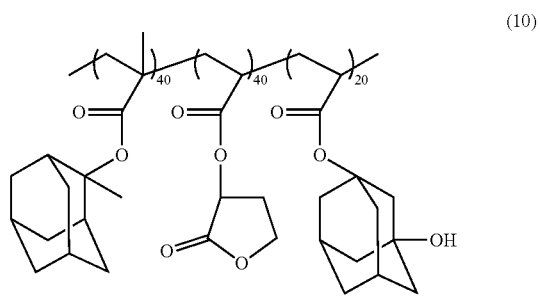

(10)

In the formula (10), the numerals 40, 40, and 20 indicate the proportions of the respective constituent units, and do not mean a block copolymer.

TABLE 1

| | SNCN (parts by mass) | CR1 (parts by mass) | Organic solvent (parts by mass) | Acid generating agent (parts by mass) | Crosslinking agent (parts by mass) | Etching resistance | Heat weight loss |
|---|---|---|---|---|---|---|---|
| Example 1 | 10 | | PGMEA 90 | | | A | A |
| Example 2 | 10 | | PGMEA 89 | DTDPI 0.5 | Nikalac 0.5 | B | A |
| Example 3 | 7 | 3 | PGMEA 89 | DTDPI 0.5 | Nikalac 0.5 | B | B |
| Example 4 | 5 | 5 | PGMEA 89 | DTDPI 0.5 | Nikalac 0.5 | B | B |
| Example 5 | 3 | 7 | PGMEA 89 | DTDPI 0.5 | Nikalac 0.5 | B | B |
| Comparative Example 1 | | 10 | PGMEA 89 | DTDPI 0.5 | Nikalac 0.5 | B | C |
| Comparative Example 2 | | 10 | PGMEA 90 | | | B | C |

Example 6

Then, the composition for forming an underlayer film for lithography in Example 1 was coated on a SiO$_2$ substrate having a film thickness of 300 nm, and baked at 240° C. for 60 seconds and further at 400° C. for 120 seconds to thereby form an underlayer film having a film thickness of 70 nm. A resist solution for ArF was coated on the underlayer film, and baked at 130° C. for 60 seconds to thereby form a photoresist layer having a film thickness of 140 nm. As the resist solution for ArF, one prepared by blending 5 parts by mass of the compound of the following formula (10), 1 part by mass of triphenylsulfonium nonafluoromethanesulfonate, 2 parts by mass of tributylamine, and 92 parts by mass of PGMEA was used.

A compound of following formula (10) was prepared as follows. That is, 4.15 g of 2-methyl-2-methacryloyloxyadamantane, 3.00 g of methacryloyloxy-γ-butyrolactone, 2.08 g of 3-hydroxy-1-adamantyl methacrylate and 0.38 g of azobisisobutyronitrile were dissolved in 80 mL of tetrahydrofuran to provide a reaction solution. This reaction solution Then, the photoresist layer was exposed by using an electron beam lithography apparatus (ELS-7500, produced by Elionix, Inc., 50 keV), baked at 115° C. for 90 seconds (PEB), and developed with a 2.38% by mass aqueous tetramethylammonium hydroxide (TMAH) solution for 60 seconds, thereby providing a positive-type resist pattern.

Example 7

Except that the composition for forming an underlayer film for lithography in Example 2 was used instead of the composition for forming an underlayer film for lithography in Example 1, the same manner as in Example 6 was performed to provide a positive-type resist pattern.

Comparative Example 3

Except that no underlayer film was formed, the same manner as in Example 6 was performed to form a photoresist layer directly on a SiO$_2$ substrate to provide a positive-type resist pattern.

[Evaluation]

The shapes of the resist patterns of 55 nm L/S (1:1) and 80 nm L/S (1:1) provided in each of Examples 6, 7 and Comparative Example 3 were observed by using an electron microscope (S-4800) manufactured by Hitachi Ltd. A case where the shape of the resist pattern after development had no pattern collapse and had good rectangularity was evaluated to be good and a case the shape had pattern collapse and did not have good rectangularity was evaluated to be poor. In the observation results, the minimum line width where there was no pattern collapse and rectangularity was good was defined as the resolution and used as an evaluation index. Furthermore, the minimum amount of electron beam energy, where a good pattern shape could be drawn, was defined as the sensitivity and used as an evaluation index. The results are shown in Table 2.

TABLE 2

| | Composition for forming underlayer film | Resolution (nmL/S) | Sensitivity ($\mu C/cm^2$) | Resist pattern shape after development |
|---|---|---|---|---|
| Example 6 | Composition described in Example 1 | 55 | 16 | Good |
| Example 7 | Composition described in Example 2 | 56 | 16 | Good |
| Comparative Example 3 | Not used | 80 | 38 | Not good |

As can be seen from Table 2, it was confirmed that Examples 6 and 7 were significantly excellent in resolution and sensitivity as compared with Comparative Example 3. It was also confirmed that the resist pattern shape after development had no pattern collapse and had good rectangularity. Furthermore, it was shown from the difference in the resist pattern shape after development that the underlayer film obtained from the composition for an underlayer film for lithography in each of Examples 6 and 7 had good adhesiveness with a resist material.

The composition for forming an underlayer film for lithography of the present invention has a relatively high heat resistance and also a relatively high solvent solubility, and can be applied to a wet process. Therefore, the composition for forming an underlayer film for lithography, and the underlayer film formed using the composition, of the present invention, can be widely and effectively utilized in various applications in which these properties are required.

The invention claimed is:

1. A composition for forming an underlayer film for lithography, comprising:
   a compound represented by the following formula (1) and 20 to 99% by mass of a solvent component (S),
   wherein 27 to 100% by mass of the compound represented by the formula (1) is comprised in a component (A) other than the solvent component (S)

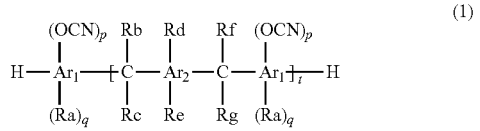

in formula (1), each $Ar_1$ independently represents a benzene structure or a naphthalene structure and each $Ar_2$ independently represents a benzene structure, a naphthalene structure or a biphenyl structure, each Ra independently represents a hydrogen atom, an alkyl group having 1 to 6 carbon atoms, an aryl group having 6 to 12 carbon atoms, an alkoxy group having 1 to 4 carbon atoms, or a group in which an alkyl group having 1 to 6 carbon atoms is bonded to an aryl group having 6 to 12 carbon atoms, each of Rb, Rc, Rf and Rg independently represents a hydrogen atom, an alkyl group having 1 to 6 carbon atoms or an aryl group having 6 to 12 carbon atoms, each of Rd and Re independently represents a hydrogen atom, an alkyl group having 1 to 6 carbon atoms, an aryl group having 6 to 12 carbon atoms, an alkoxy group having 1 to 4 carbon atoms or a hydroxy group, wherein a position of a substituent on each of $Ar_1$ and $Ar_2$ can be arbitrarily selected, p represents the number of cyanate group(s) bonded and is an integer of 1 to 3, q represents the number of Ra bonded and is 4−p when $Ar_1$ represents the benzene structure, 6−p when $Ar_1$ represents the naphthalene structure, or 8−p when $Ar_1$ represents the biphenyl structure, and t represents an integer of 1 to 50, wherein component (A) further comprises an acid generating agent.

2. The composition for forming the underlayer film for lithography according to claim 1, wherein the compound represented by the formula (1) is a compound represented by the following formula (2)

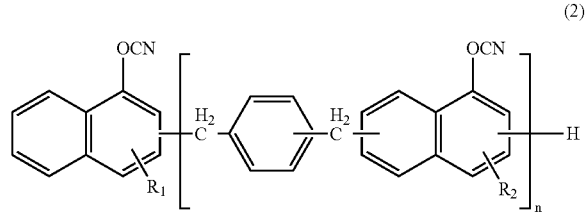

in formula (2), each of $R_1$ and $R_2$ independently represents a hydrogen atom or an alkyl group having 1 to 6 carbon atoms, and may be the same or different, wherein a position of each of $R_1$ and $R_2$ on the aromatic ring can be arbitrarily selected, and n represents an integer of 1 to 50.

3. The composition for forming the underlayer film for lithography according to claim 2, wherein the compound represented by the formula (2) is a compound represented by the following formula (5)

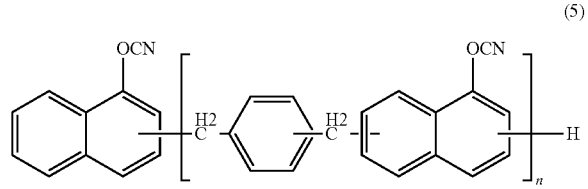

in formula (5), n represents an integer of 1 to 50.

4. The composition for forming the underlayer film for lithography according to claim 1, wherein the compound represented by the formula (1) is a compound represented by the following formula (3)

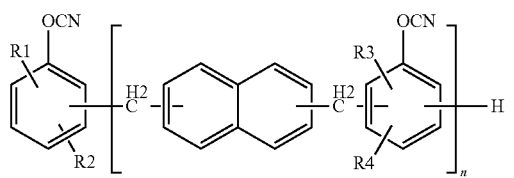

(3)

in formula (3), each of $R_1$ to $R_4$ independently represents a hydrogen atom or an alkyl group having 1 to 6 carbon atoms, and may be the same or different, and n represents an integer of 1 to 50.

5. The composition for forming the underlayer film for lithography according to claim 4, wherein the compound represented by the formula (3) is a compound represented by the following formula (6)

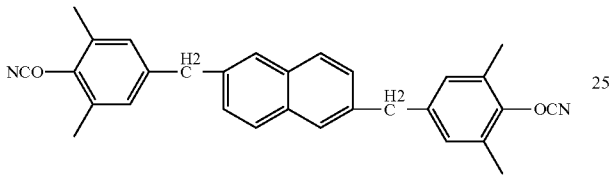

(6)

6. The composition for forming the underlayer film for lithography according to claim 1, wherein the compound represented by the formula (1) is a compound represented by the following formula (4)

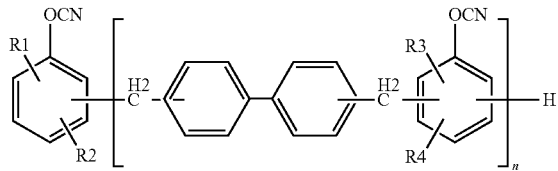

(4)

in formula (4), each of $R_1$ to $R_4$ independently represents a hydrogen atom or an alkyl group having 1 to 6 carbon atoms, and may be the same or different, and n represents an integer of 1 to 50.

7. The composition for forming the underlayer film for lithography according to claim 6, wherein the compound represented by the formula (4) is a compound represented by the following formula (7)

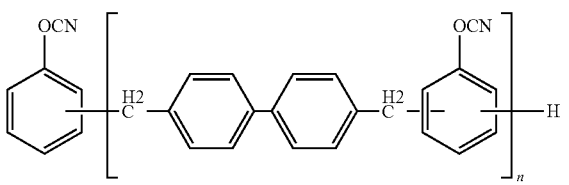

(7)

in formula (7), n represents an integer of 1 to 50.

8. The composition for forming the underlayer film for lithography according to claim 1, wherein the component (A) further comprises a crosslinking agent.

9. An underlayer film for lithography, formed by coating the composition for forming the underlayer film for lithography according to claim 1.

10. A resist pattern forming method comprising
   step (A-1) of forming an underlayer film on a substrate by coating the composition for forming the underlayer film according to claim 1,
   step (A-2) of forming at least one photoresist layer on the underlayer film, and
   step (A-3) of, after step (A-2), irradiating a predetermined region of the photoresist layer with radiation, followed by developing.

11. A circuit pattern forming method comprising
   step (B-1) of forming an underlayer film on a substrate by coating the composition for forming the underlayer film according to claim 1,
   step (B-2) of forming an intermediate layer film on the underlayer film by using a silicon atom-containing resist intermediate layer film material,
   step (B-3) of forming at least one photoresist layer on the intermediate layer film,
   step (B-4) of, after step (B-3), irradiating a predetermined region of the photoresist layer with radiation, followed by developing to form a resist pattern, and
   step (B-5) of, after step (B-4), etching the intermediate layer film with the resist pattern as a mask, etching the underlayer film with an obtained intermediate layer film pattern as an etching mask and etching the substrate with an obtained underlayer film pattern as an etching mask, to form a pattern on the substrate.

\* \* \* \* \*

UNITED STATES PATENT AND TRADEMARK OFFICE
CERTIFICATE OF CORRECTION

PATENT NO. : 10,338,471 B2
APPLICATION NO. : 15/502456
DATED : July 2, 2019
INVENTOR(S) : Kana Okada et al.

Page 1 of 1

It is certified that error appears in the above-identified patent and that said Letters Patent is hereby corrected as shown below:

In the Claims

Column 38, Line (17):
In Claim 1, please delete "Ar₁and" and insert -- Ar₁ and --, therefor.

Column 38, Line (20):
In Claim 1, please delete "Ar₁represents" and insert -- Ar₁ represents --, therefor.

Column 39, Line (26):

In Claim 5, after " 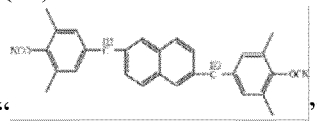 " insert -- . --.

Signed and Sealed this
Thirty-first Day of December, 2019

Andrei Iancu
*Director of the United States Patent and Trademark Office*